United States Patent
Avory

(10) Patent No.: US 8,894,971 B2
(45) Date of Patent: Nov. 25, 2014

(54) IODINE RADIOLABELLING METHOD

(75) Inventor: Michelle Avory, Amersham (GB)

(73) Assignee: GE Healthcare Limited, Buckinghamshire (GB)

(*) Notice: Subject to any disclaimer, the term of this patent is extended or adjusted under 35 U.S.C. 154(b) by 72 days.

(21) Appl. No.: 13/510,656

(22) PCT Filed: Dec. 10, 2010

(86) PCT No.: PCT/EP2010/069341
§ 371 (c)(1),
(2), (4) Date: May 18, 2012

(87) PCT Pub. No.: WO2011/070136
PCT Pub. Date: Jun. 16, 2011

(65) Prior Publication Data
US 2012/0237444 A1    Sep. 20, 2012

Related U.S. Application Data

(60) Provisional application No. 61/285,199, filed on Dec. 10, 2009.

(30) Foreign Application Priority Data

Dec. 10, 2009 (GB) .................................. 0921573.2

(51) Int. Cl.
| A61K 51/08 | (2006.01) |
| A61K 51/04 | (2006.01) |
| C07B 59/00 | (2006.01) |
| C07C 247/16 | (2006.01) |
| C07C 291/06 | (2006.01) |
| C07D 231/12 | (2006.01) |
| C07D 249/06 | (2006.01) |
| C07D 261/08 | (2006.01) |
| C07K 1/13 | (2006.01) |
| C07K 5/09 | (2006.01) |

(52) U.S. Cl.
CPC .............. *A61K 51/08* (2013.01); *C07B 59/002* (2013.01); *C07C 247/16* (2013.01); *C07C 291/06* (2013.01); *C07D 231/12* (2013.01); *C07D 249/06* (2013.01); *C07D 261/08* (2013.01); *C07K 1/13* (2013.01); *C07K 5/0817* (2013.01); *C07B 2200/05* (2013.01); *G01N 2800/52* (2013.01)
USPC ........ 424/1.69; 424/1.11; 424/1.65; 424/1.89

(58) Field of Classification Search
USPC ........... 424/1.11, 1.41, 1.49, 1.53, 1.65, 1.69, 424/1.73, 1.81, 1.85, 1.89, 9.1, 9.2, 9.3, 9.4, 424/9.5, 9.6, 9.7, 9.8; 534/7, 10–16
See application file for complete search history.

(56) References Cited

U.S. PATENT DOCUMENTS 7,972,588 B2 * 7/2011 Arstad et al. ................. 424/1.69

FOREIGN PATENT DOCUMENTS

| WO | 2006/067376 | 6/2006 |
| WO | 2006/116629 | 11/2006 |
| WO | 2007/148089 | 12/2007 |
| WO | 2008/131148 | 10/2008 |

OTHER PUBLICATIONS

Johnstrom, et.al. Nuclear Medicine and Biology, vol. 35, No. 6, Aug. 1, 2008 pp. 725-731.
Dong, et.al. Chembiochem—A European Journal of Chemical Biology, vol. 10, No. 7, May 1, 2009 pp. 1149-1151.
Thonon, et.al. Bioconjugate Chemistry vol. 20, No. 4, Apr. 15, 2009, pp. 817-823.
Qu, et.aol. Journal of Medicinal Chemistry, vol. 50, No. 14, Jan. 1, 2007, pp. 3380-3387.
PCT/EP2010/069341 ISRWO Dated Mar. 30, 2011.
GB0921573.2 Search Report Dated Jun. 7, 2010.

* cited by examiner

*Primary Examiner* — Michael G Hartley
*Assistant Examiner* — Jagadishwar Samala

(57) ABSTRACT

The present invention provides a novel method of labelling biological targeting molecules (BTMs) of interest with radioiodine. Also provided are novel radioiodinated BTMs prepared using the method, as well as radiopharmaceutical compositions comprising such radioiodinated BTMs. The invention also provides radioiodinated intermediates useful in the method, as well as in vivo imaging methods using the radioiodinated BTMs.

5 Claims, No Drawings

SEQUENCE LISTING

```
<160> NUMBER OF SEQ ID NOS: 9

<210> SEQ ID NO 1
<211> LENGTH: 5
<212> TYPE: PRT
<213> ORGANISM: Artificial
<220> FEATURE:
<223> OTHER INFORMATION: synthetic peptide

<400> SEQUENCE: 1

Tyr Ile Gly Ser Arg
1               5

<210> SEQ ID NO 2
<211> LENGTH: 5
<212> TYPE: PRT
<213> ORGANISM: Artificial
<220> FEATURE:
<223> OTHER INFORMATION: synthetic peptide

<400> SEQUENCE: 2

Pro Asp Ser Gly Arg
1               5

<210> SEQ ID NO 3
<211> LENGTH: 5
<212> TYPE: PRT
<213> ORGANISM: Artificial
<220> FEATURE:
<223> OTHER INFORMATION: synthetic peptide
```

```
<400> SEQUENCE: 3

Ile Lys Val Ala Val
1               5

<210> SEQ ID NO 4
<211> LENGTH: 3
<212> TYPE: PRT
<213> ORGANISM: Artificial
<220> FEATURE:
<223> OTHER INFORMATION: synthetic peptide

<400> SEQUENCE: 4

Leu Arg Glu
1

<210> SEQ ID NO 5
<211> LENGTH: 15
<212> TYPE: PRT
<213> ORGANISM: Artificial
<220> FEATURE:
<223> OTHER INFORMATION: synthetic peptide

<400> SEQUENCE: 5

Lys Cys Gln Ala Gly Thr Phe Ala Leu Arg Gly Asp Pro Gln Gly
1               5                   10                  15

<210> SEQ ID NO 6
<211> LENGTH: 3
<212> TYPE: PRT
<213> ORGANISM: Artificial
<220> FEATURE:
<223> OTHER INFORMATION: synthetic peptide

<400> SEQUENCE: 6

Arg Gly Asp
1

<210> SEQ ID NO 7
<211> LENGTH: 8
<212> TYPE: PRT
<213> ORGANISM: Artificial
<220> FEATURE:
<223> OTHER INFORMATION: synthetic peptide

<400> SEQUENCE: 7

Asp Arg Val Tyr Ile His Pro Phe
1               5

<210> SEQ ID NO 8
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Sar

<400> SEQUENCE: 8

Xaa Arg Val Tyr Ile His Pro Ile
1               5

<210> SEQ ID NO 9
<211> LENGTH: 8
<212> TYPE: PRT
<213> ORGANISM: Artificial
```

```
<220> FEATURE:
<223> OTHER INFORMATION: synthetic peptide
<220> FEATURE:
<221> NAME/KEY: THIOETH
<222> LOCATION: (1)..(8)
<220> FEATURE:
<221> NAME/KEY: DISULFID
<222> LOCATION: (2)..(6)

<400> SEQUENCE: 9

Lys Cys Arg Gly Asp Cys Phe Cys
1               5
```

IODINE RADIOLABELLING METHOD

This application is a filing under 35 U.S.C. 371 of international application number PCT/EP2010/069341, filed Dec. 10, 2010, which claims priority to Great Britain application number 0921573.2 filed Dec. 10, 2009 and U.S. application No. 61/285,199 filed Dec. 10, 2009, the entire disclosure of which is hereby incorporated by reference.

FIELD OF THE INVENTION

The present invention provides a novel method of labelling biological targeting molecules (BTMs) of interest with radioiodine. Also provided are novel radioiodinated BTMs prepared using the method, as well as radiopharmaceutical compositions comprising such radioiodinated BTMs. The invention also provides radioiodinated intermediates useful in the method, as well as in vivo imaging methods using the radioiodinated BTMs.

BACKGROUND TO THE INVENTION

Methods of incorporating radiohalogens into organic molecules are known [Bolton, J. Lab. Comp. Radiopharm., 45, 485-528 (2002)]. For the case of $^{123}$I-labelled radiopharmaceuticals, Eersels et al [J. Lab. Comp. Radiopharm., 48, 241-257 (2005)] have compared the 4 principal synthetic routes:
  (i) oxidative radioiodination;
  (ii) nucleophilic isotopic exchange;
  (iii) nucleophilic non-isotopic exchange;
  (iv) electrophilic labelling.
Route (iv) typically involves the use of an organometallic precursors, such as trialkyltin, trialkylsilyl or organomercury or organothallium derivative. Of these, the radioiododestannylation route was acknowledged as having become the preferred electrophilic labelling method, due to the possibility of regiospecific radioiodination at room temperature. Eersels et al concluded, however, that there was no overall preferred radioiodination method, since the choice depends on the nature of the compound to be radioiodinated.

The use of organotin intermediates in radiopharmaceutical synthesis has been reviewed by Ali et al [Synthesis, 423-445 (1996)]. Kabalka et al have published extensively on the use of organoborane precursors to permit radioisotope and radiohalogen labelling [see eg. J. Lab. Comp. Radiopharm., 50, 446-447 and 888-894 (2007)].

Click chemistry is a growing area of biotechnology research ["Click Chemistry for Biotechnology and Materials Science", J. Lahann (Ed), Wily, (2009)]. Hein et al have reported that 1-iodoalkynes undergo click cyclisation reactions with azides as follows [Ang. Chem. Int. Ed. Engl., 48, 8018-8021 (2009)]:

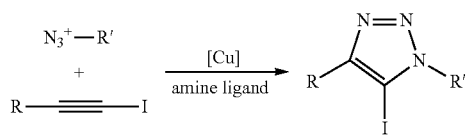

Hein is concerned with internal alkynes (ie. R is not H), and is silent on radiochemistry.

The applications of "click chemistry" in biomedical research, including radiochemistry, have been reviewed by Nwe et al [Cancer Biother. Radiopharm., 24(3), 289-302 (2009)]. As noted therein, the main interest has been in the PET radioisotope $^{18}$F (and to a lesser extent $^{11}$C), plus "click to chelate" approaches for radiometals suitable for SPECT imaging such as $^{99m}$Tc or $^{111}$In. Glaser and Robins have reviewed the use of click chemistry in PET radiochemical labelling reactions, focusing on the radioisotopes $^{18}$F and $^{11}$C [J. Lab. Comp. Radiopharm., 52, 407-414 (2009)].

$^{18}$F click-labelling of targeting peptides, giving products incorporating an $^{18}$F-fluoroalkyl-substituted triazole have been reported by Li et al [Bioconj. Chem., 18(6), 1987-1994 (2007)], and Hausner et al [J. Med. Chem., 51(19), 5901-5904 (2008)].

WO 2006/067376 discloses a method for labelling a vector comprising reaction of a compound of formula (I) with a compound of formula (II):

 (I)

 (II)

or, a compound of formula (III) with a compound of formula (IV):

 (III)

 (IV)

in the presence of a Cu(I) catalyst, wherein:
  L1, L2, L3, and L4 are each Linker groups;
  R* is a reporter moiety which comprises a radionuclide;
to give a conjugate of formula (V) or (VI) respectively:

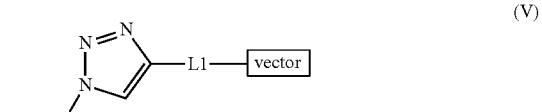 (V)

 (VI)

R* of WO 2006/067376 is a reporter moiety which comprises a radionuclide, e.g. a positron-emitting radionuclide. Suitable positron-emitting radionuclides for this purpose are said to include $^{11}$C, $^{18}$F, $^{75}$Br, $^{76}$Br, $^{124}$I, $^{82}$Rb, $^{68}$Ga, $^{64}$Cu and $^{62}$Cu, of which $^{11}$C and $^{18}$F are preferred. Other useful radionuclides are stated to include $^{123}$I, $^{125}$I, $^{131}$I, $^{211}$At, $^{99m}$Tc, and $^{111}$In.

WO 2007/148089 discloses a method for radiolabelling a vector comprising reaction of a compound of formula (I) with a compound of formula (II):

 (I)

 (II)

or, a compound of formula (III) with a compound of formula (IV):

(III)

R*-L4-≡ (IV)

in the presence of a Cu(I) catalyst, wherein:
L1, L2, L3, and L4 are each Linker groups;
R* is a reporter moiety which comprises a radionuclide;
to give a conjugate of formula (V) or (VI) respectively:

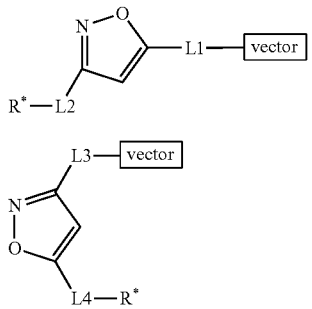

(V)

(VI)

In both WO 2006/067376 and WO 2007/148089, metallic radionuclides are stated to be suitably incorporated into a chelating agent, for example by direct incorporation by methods known to the person skilled in the art. Neither WO 2006/067376 nor WO 2007/148089 discloses any methodology specific for click radioiodination—in particular which combination of compounds of formulae (I)-(IV), together with which combinations of linker groups L1, L2, L3, L4, and which type of R* group would be suitable.

WO 2006/116629 (Siemens Medical Solutions USA, Inc.) discloses a method of preparation of a radiolabelled ligand or substrate having affinity for a target biomacromolecule, the method comprising:
(a) reacting a first compound comprising
  (i) a first molecular structure;
  (ii) a leaving group;
  (iii) a first functional group capable of participating in a click chemistry reaction; and optionally,
  (iv) a linker between the first functional group and the molecular structure, with a radioactive reagent under conditions sufficient to displace the leaving group with a radioactive component of the radioactive reagent to form a first radioactive compound;
(b) providing a second compound comprising
  (i) a second molecular structure;
  (ii) a second complementary functional group capable of participating in a click chemistry reaction with the first functional group, wherein the second compound optionally comprises a linker between the second compound and the second functional group;
(c) reacting the first functional group of the first radioactive compound with the complementary functional group of the second compound via a click chemistry reaction to form the radioactive ligand or substrate; and
(d) isolating the radioactive ligand or substrate.

WO 2006/116629 teaches that the method therein is suitable for use with the radioisotopes: $^{124}$I, $^{18}$F, $^{11}$C, $^{13}$N and $^{15}$O with preferred radioisotopes being: $^{18}$F, $^{11}$C, $^{123}$I, $^{124}$I, $^{127}$I, $^{131}$I, $^{76}$Br, $^{64}$Cu, $^{99m}$Tc, $^{90}$Y, $^{67}$Ga, $^{51}$Cr, $^{192}$Ir, $^{99}$Mo, $^{153}$Sm and $^{201}$Tl. WO 2006/116629 teaches that other radioisotopes that may be employed include: $^{72}$As, $^{74}$As, $^{75}$Br, $^{55}$Co, $^{61}$Cu, $^{67}$Cu, $^{68}$Ga, $^{68}$Ge, $^{125}$I, $^{132}$I, $^{111}$In, $^{52}$Mn, $^{203}$Pb and $^{97}$Ru. WO 2006/116629 does not, however, provide any specific teaching on how to apply the method to the radioiodination of biological molecules.

Qu et al [J. Med. Chem., 50(14), 3380-3387 (2007)] disclose the preparation of $^{125}$I-labelled amines:

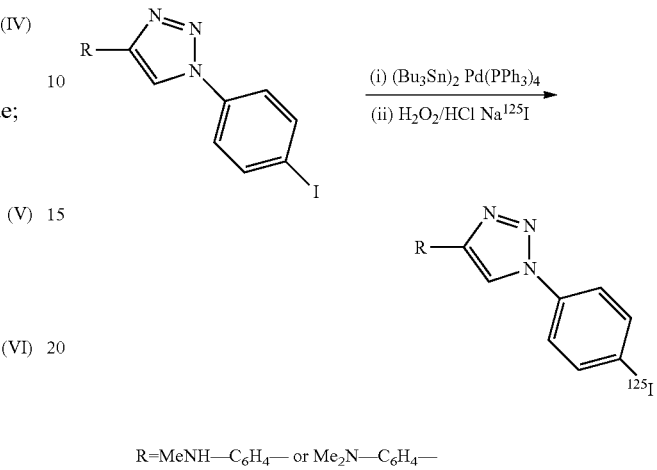

R=MeNH—C$_6$H$_4$— or Me$_2$N—C$_6$H$_4$—

The non-radioactive iodophenyl-triazole precursor is prepared via click cyclisation of R—≡—H and I—C$_6$H$_4$—N$_3$. WO 2008/131148 is a corresponding patent application by Qu et al which discloses similar chemistry.

Dong et al [ChemBioChem, 10, 1149-1151 (2009)] disclose a method of iodinating proteins using click chemistry:

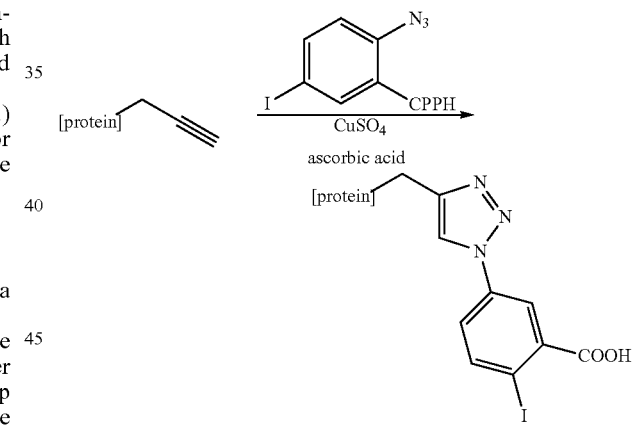

Dong et al introduced the alkyne group into the protein using the synthetic amino acid homopropargylglycine in place of the N-terminus Met residue. The protein studied is engineered to be cysteine-free, and consists of 90 amino acids. Dong et al suggest that the method could usefully be applied to radioimmunoassay using the radioisotope $^{125}$I, but no radioactive chemistry is described.

WO 2010/131745 discloses $^{18}$F-labelled phenylazides of formula shown, and their use to radiolabel alkyne-functionalised oligonucleotides via click cycloaddition, forming triazole rings:

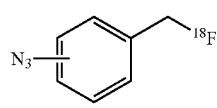

There is therefore still a need for alternative radioiodination methods, which provide radioiodinated biological targeting molecules suitable for in vivo imaging, with the iodine label in a chemical form which is resistant to in vivo metabolic deiodination.

The Present Invention.

The present invention provides methodology for the radioiodination of biological targeting molecules (BTMs), using click radioiodination. The method has the advantage that it can be carried out under mild conditions, and is hence compatible with a range of biological molecules—potentially including such molecules where conventional direct radioiodination methods may be non-viable due to instability of the BTM under the radioiodination reaction conditions. Examples of such sensitivity includes incompatibility or instability with the oxidising conditions necessary for conventional radioiodination. The present method provides radioiodination methodology which can be carried out under non-oxidising conditions, and is hence particularly advantageous for labelling BTMs which are susceptible to oxidation.

The click cyclisation used in the present method is highly selective, hence the radioiodine labelling occurs regioselectively at the alkyne group of the functionalised BTM of Formula I. The method provides products in which the radioiodine is directly bonded to a group ($Y^1$), which is chosen to be resistant to in vivo metabolism of the carbon-iodine bond. The radioiodinated products are thus expected to exhibit good stability with respect to metabolic deiodination in vivo, with consequent unwanted stomach and/or thyroid uptake of radioiodine. The products are therefore suitable for use as radiopharmaceuticals for in vivo imaging, which is an important advantage.

The click radioiodination methodology is readily adaptable to use with an automated synthesizer apparatus. Due to its selectivity, it can also permit BTM labelling without the need to use protecting groups. In addition, the labelling has the potential to achieve higher radiolabelling yields than conventional conjugation reactions using e.g. active ester coupling.

DETAILED DESCRIPTION OF THE INVENTION

In a first aspect, the present invention provides a method of radioiodination of a biological targeting moiety, said method comprising:

(i) provision of a compound of Formula (I):

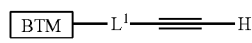
(I)

(ii) reaction of said compound of Formula (I) with a compound of Formula (IIa) or Formula (IIb):

 (IIa)

 (IIb)

in the presence of a click cycloaddition catalyst, to give a conjugate of Formula (IIIa) or (IIIb) respectively:

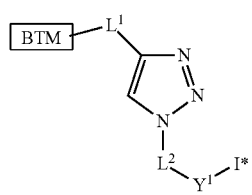
(IIIa)

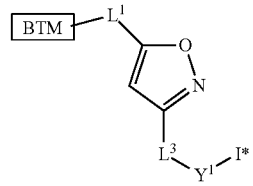
(IIIb)

wherein:
$I^*$ is a radioisotope of iodine, suitable for in vivo imaging chosen from $^{123}I$, $^{124}I$ or $^{131}I$;
$L^1$, $L^2$ and $L^3$ are each independently a linker group which may be present or absent;
$Y^1$ is —$Ar^1$— or —$X^1$—;
where —$Ar^1$— is $C_{3-10}$ arylene, and
—$X^1$— is —CH=CH—$(CH_2)_n$—$(Ar^1)_j$— or —CH=CH—$(Ar^1)_j$—$(CH_2)_n$—
where j is 0 or 1, and n is an integer of value 0 to 4,
wherein when $Y^1$ is —$X^1$—, $I^*$ is attached to —CH=CH terminus of $X^1$; BTM is the biological targeting moiety.

The term "radioiodination" has its conventional meaning, i.e. a radiolabelling process wherein the radioisotope used for the radiolabelling is a radioisotope of iodine.

When the linker group ($L^1$) is absent, that means that the alkyne group of Formula (I) is bonded directly to the BTM. That could mean for example, that the alkyne is conjugated to the side chain of an amino acid of a BTM peptide or protein, or directly to the N- or C-terminus of a BTM peptide. When present, each linker group ($L^1$) is preferably synthetic, and independently comprises a group of formula -$(A)_m$- wherein each A is independently —$CR_2$—, —CR=CR—, —C≡C—, —$CR_2CO_2$—, —$CO_2CR_2$—, —NRCO—, —CONR—, —NR(C=O)NR—, —NR(C=S)NR—, —$SO_2NR$—, —$NRSO_2$—, —$CR_2OCR_2$—, —$CR_2SCR_2$—, —$CR_2NRCR_2$—, a $C_{4-8}$ cycloheteroalkylene group, a $C_{4-8}$ cycloalkylene group, a $C_{5-12}$ arylene group, or a $C_{3-12}$ heteroarylene group, an amino acid, a sugar or a monodisperse polyethyleneglycol (PEG) building block;

wherein each R is independently chosen from: H, $C_{1-4}$ alkyl, $C_{2-4}$ alkenyl, $C_{2-4}$ alkynyl, $C_{1-4}$ alkoxyalkyl or $C_{1-4}$ hydroxyalkyl;

and m is an integer of value 1 to 20.

By the term "biological targeting moiety" (BTM) is meant a compound which, after administration, is taken up selectively or localises at a particular site of the mammalian body in vivo. Such sites may for example be implicated in a particular disease state or be indicative of how an organ or metabolic process is functioning.

The term radioisotope of iodine has its conventional meaning, i.e. an isotope of the element iodine that is radioactive. Such radioisotopes which are suitable for in vivo imaging are: $^{123}I$, $^{124}I$, and $^{131}I$. $^{125}I$ is not suitable for in vivo imaging, and is thus outside the scope of the present claims. The radioiodinated product is useful as a radiopharmaceutical for diagnostic imaging or therapeutic applications in vivo. Such therapeutic applications include radioimmunotherapy when the BTM is an antibody or antibody fragment. $^{131}I$ is a preferred radioisotope for therapeutic applications in vivo.

By the term "click cycloaddition catalyst" is meant a catalyst known to catalyse the click (alkyne plus azide) or click (alkyne plus isonitrile oxide) cycloaddition reaction of the first aspect. Suitable such catalysts are known in the art for use in click cycloaddition reactions. Preferred such catalysts include Cu(I), and are described below. Further details of suitable catalysts are described by Wu and Fokin [Aldrichim. Acta, 40(1), 7-17 (2007)] and Meldal and Tornoe [Chem. Rev., 108, 2952-3015 (2008)].

By the term "$C_{3-10}$ arylene" is meant a bivalent aryl radical having 3 to 10 carbon atoms. The term encompasses carbon-containing and heteroaryl groups. Suitable such heteroaryl groups include pyridine, indole or imidazole rings. In Formulae (IIa) or (IIb) the radioiodine isotope (I*) is bonded directly to the aryl ring or vinyl group of $Y^1$.

When $Y^1$ is $X^1$, the phrase "I* is attached to —CH=CH terminus of $X^{1}$" means that the compound of Formula (IIa) is: I*—CH=CH—$(CH_2)_n$—$(Ar^1)_m$—$N_3$ or I*—CH=CH—$(Ar^1)_m$—$(CH_2)_n$—$N_3$ where m is 0 or 1, and n is an integer of value 0 to 4. Similar logic applies to compounds (IIb), (IIIa) and (IIIb).

Preferred Aspects.

A preferred precursor for use in the method of the first aspect is the azide of Formula (IIa), and hence a preferred product is the triazole of Formula (IIIa).

Preferred radioisotopes of iodine for use in the present invention are those suitable for medical imaging in vivo using PET or SPECT. Thus, I* is preferably $^{123}I$ or $^{124}I$, where $^{123}I$ is suitable for SPECT imaging and $^{124}I$ for PET imaging. I* is most preferably $^{123}I$.

The $Y^1$ group is conjugated directly to I*, and the $Y^1$—I* bond is part of the product of Formula (IIIa) or (IIIb). The $Y^1$ groups of the present invention are thus designed to give products wherein the radioiodine label (i.e. I*) is not susceptible to in vivo deiodination. When $Y^1$ is $Ar^1$, a preferred $Ar^1$ group is $C_{4-6}$ arylene, more preferably comprising a substituted or unsubstituted phenyl or pyridine ring, most preferably a phenylene ring. When $Y^1$ is $X^1$, the vinyl group may be in the E- or Z-orientation, i.e. both diastereomers are within the scope of the present invention. $X^1$ is preferably chosen such that n is 1 to 4, more preferably n is 1 to 4 and j is 0. $Y^1$ is preferably $Ar^1$, including the preferred $Ar^1$ groups as defined above.

The BTM may be of synthetic or natural origin, but is preferably synthetic. The term "synthetic" has its conventional meaning, i.e. man-made as opposed to being isolated from natural sources eg. from the mammalian body. Such compounds have the advantage that their manufacture and impurity profile can be fully controlled. Monoclonal antibodies and fragments thereof of natural origin are therefore outside the scope of the term 'synthetic' as used herein. The BTM is preferably non-proteinaceous, i.e. does not comprise a protein.

The molecular weight of the BTM is preferably up to 10,000 Daltons. More preferably, the molecular weight is in the range 200 to 9,000 Daltons, most preferably 300 to 8,000 Daltons, with 400 to 6,000 Daltons being especially preferred. When the BTM is a non-peptide, the molecular weight of the BTM is preferably up to 3,000 Daltons, more preferably 200 to 2,500 Daltons, most preferably 300 to 2,000 Daltons, with 400 to 1,500 Daltons being especially preferred.

The biological targeting moiety preferably comprises: a 3-80 mer peptide, peptide analogue, peptoid or peptide mimetic which may be a linear or cyclic peptide or combination thereof; a single amino acid; an enzyme substrate, enzyme antagonist enzyme agonist (including partial agonist) or enzyme inhibitor; receptor-binding compound (including a receptor substrate, antagonist, agonist or substrate); oligonucleotides, or oligo-DNA or oligo-RNA fragments.

By the term "peptide" is meant a compound comprising two or more amino acids, as defined below, linked by a peptide bond (i.e. an amide bond linking the amine of one amino acid to the carboxyl of another). The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. The term "peptide analogue" refers to peptides comprising one or more amino acid analogues, as described below. See also *Synthesis of Peptides and Peptidomimetics*, M. Goodman et al, Houben-Weyl Vol E22c of 'Methods in Organic Chemistry', Thieme (2004).

By the term "amino acid" is meant an L- or D-amino acid, amino acid analogue (eg. naphthylalanine) or amino acid mimetic which may be naturally occurring or of purely synthetic origin, and may be optically pure, i.e. a single enantiomer and hence chiral, or a mixture of enantiomers. Conventional 3-letter or single letter abbreviations for amino acids are used herein. Preferably the amino acids of the present invention are optically pure. By the term "amino acid mimetic" is meant synthetic analogues of naturally occurring amino acids which are isosteres, i.e. have been designed to mimic the steric and electronic structure of the natural compound. Such isosteres are well known to those skilled in the art and include but are not limited to depsipeptides, retro-inverso peptides, thioamides, cycloalkanes or 1,5-disubstituted tetrazoles [see M. Goodman, Biopolymers, 24, 137, (1985)]. Radiolabelled amino acids such as tyrosine, histidine, methionine or proline are known to be useful in vivo imaging agents.

When the BTM is an enzyme substrate, enzyme antagonist, enzyme agonist, enzyme inhibitor or receptor-binding compound it is preferably a non-peptide, and more preferably is synthetic. By the term "non-peptide" is meant a compound which does not comprise any peptide bonds, i.e. an amide bond between two amino acid residues. Suitable enzyme substrates, antagonists, agonists or inhibitors include glucose and glucose analogues such as fluorodeoxyglucose; fatty acids, or elastase, Angiotensin II or metalloproteinase inhibitors. A preferred non-peptide Angiotensin II antagonist is Losartan. Suitable synthetic receptor-binding compounds include estradiol, estrogen, progestin, progesterone and other steroid hormones; ligands for the dopamine D-1 or D-2 receptor, or dopamine transporter such as tropanes; and ligands for the serotonin receptor.

The BTM is most preferably a 3-100 mer peptide or peptide analogue. When the BTM is a peptide, it is preferably a 4-30 mer peptide, and most preferably a 5 to 28-mer peptide.

When the BTM is an enzyme substrate, enzyme antagonist, enzyme agonist or enzyme inhibitor, preferred such biological targeting molecules of the present invention are synthetic, drug-like small molecules i.e. pharmaceutical molecules. Preferred dopamine transporter ligands such as tropanes; fatty acids; dopamine D-2 receptor ligands; benzamides; amphetamines; benzylguanidines, iomazenil, benzofuran (IBF) or hippuric acid. Preferred tropane derivatives are $^{123}I$-CIT (Dopascan™), $^{123}I$-CIT-FP (DaTSCAN™) and the E isomer of $^{123}I$-2β-carbomethoxy-3β-(4-fluorophenyl)-N-(1-iodoprop-1-en-3-yl)nortropane (Altropane™) Dopascan™ and DaTSCAN™ are especially preferred. These and other tropane agents are described by Morgan and Nowotnik [Drug News Perspect., 12(3), 137-145 (1999). Preferred fatty acids are $^{123}I$-BMIPP and $^{123}I$-IPPA. Preferred amphetamine derivatives are $^{123}I$-IMP. A preferred benzylguanidine is meta-iodobenzylguanidine (MIBG), ie. $^{123}I$-MIBG.

When the BTM is a peptide, preferred such peptides include:

somatostatin, octreotide and analogues,
peptides which bind to the ST receptor, where ST refers to the heat-stable toxin produced by *E. coli* and other micro-organisms;
bombesin;
vasoactive intestinal peptide;
neurotensin;
laminin fragments eg. YIGSR, PDSGR, IKVAV, LRE and KCQAGTFALRGDPQG,
N-formyl chemotactic peptides for targeting sites of leucocyte accumulation,
Platelet factor 4 (PF4) and fragments thereof,
RGD (Arg-Gly-Asp)-containing peptides, which may eg. target angiogenesis [R. Pasqualini et al., Nat. Biotechnol. 1997 June; 15(6):542-6]; [E. Ruoslahti, Kidney Int. 1997 May; 51(5):1413-7].
peptide fragments of α$_2$-antiplasmin, fibronectin or beta-casein, fibrinogen or thrombospondin. The amino acid sequences of α$_2$-antiplasmin, fibronectin, beta-casein, fibrinogen and thrombospondin can be found in the following references: α$_2$-antiplasmin precursor [M. Tone et al., J. Biochem, 102, 1033, (1987)]; beta-casein [L. Hansson et al, Gene, 139, 193, (1994)]; fibronectin [A. Gutman et al, FEBS Lett., 207, 145, (1996)]; thrombospondin-1 precursor [V. Dixit et al, Proc. Natl. Acad. Sci., USA, 83, 5449, (1986)]; R. F. Doolittle, Ann. Rev. Biochem., 53, 195, (1984);
peptides which are substrates or inhibitors of angiotensin, such as:
angiotensin II Asp-Arg-Val-Tyr-Ile-His-Pro-Phe (E. C. Jorgensen et al, *J. Med. Chem.*, 1979, Vol 22, 9, 1038-1044)
[Sar, Ile] Angiotensin II: Sar-Arg-Val-Tyr-Ile-His-Pro-Ile (R. K. Turker et al., *Science*, 1972, 177, 1203).
Angiotensin I: Asp-Arg-Val-Tyr-Ile-His-Pro-Phe-His-Leu.

Preferred BTM peptides are RGD peptides. A more preferred such RGD peptide comprises the fragment:

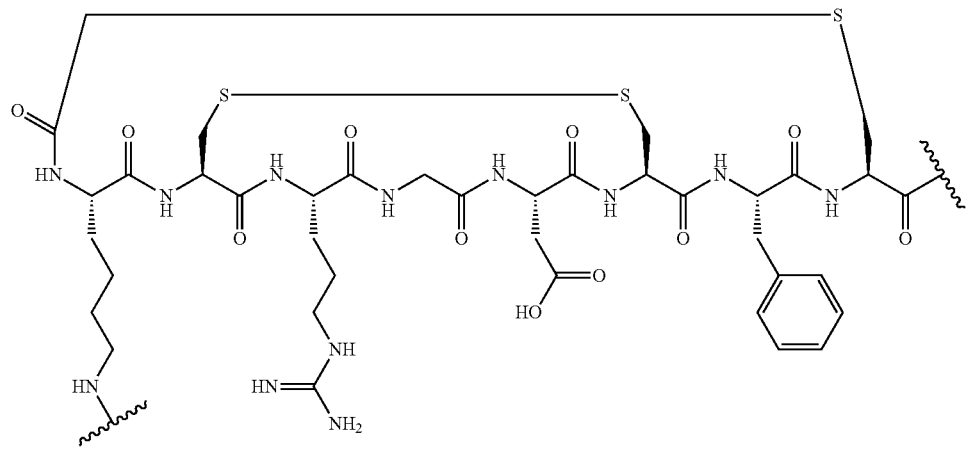 [SMILES: *NCCCC[C@@H]1NC(=O)CSC[C@@H](C(*)=O)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2]

A most preferred such RGD peptide is when the BTM is a peptide of formula (A):

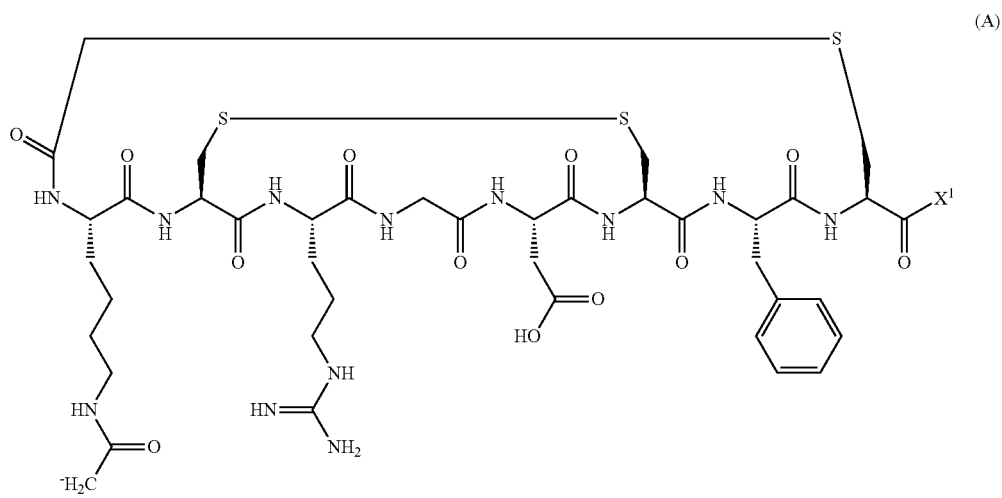

(A)

wherein $X^1$ is either —$NH_2$ or

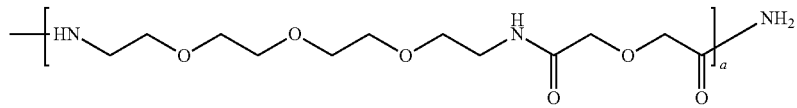

wherein a is an integer of from 1 to 10.

In Formula A, a is preferably 1.

When the BTM is a peptide, one or both termini of the peptide, preferably both, have conjugated thereto a metabolism inhibiting group ($M^{IG}$). Having both peptide termini protected in this way is important for in vivo imaging applications, since otherwise rapid metabolism would be expected with consequent loss of selective binding affinity for the BTM peptide. By the term "metabolism inhibiting group" ($M^{IG}$) is meant a biocompatible group which inhibits or suppresses enzyme, especially peptidase such as carboxypeptidase, metabolism of the BTM peptide at either the amino terminus or carboxy terminus. Such groups are particularly important for in vivo applications, and are well known to those skilled in the art and are suitably chosen from, for the peptide amine terminus:

N-acylated groups —NH(C═O)$R^G$ where the acyl group —(C═O)$R^G$ has $R^G$ chosen from: $C_{1-6}$ alkyl, $C_{3-10}$ aryl groups or comprises a polyethyleneglycol (PEG) building block. Suitable PEG groups are described for the linker group ($L^1$), below. Preferred such PEG groups are the biomodifiers of Formulae Bio1 or Bio2 (below). Preferred such amino terminus $M^{IG}$ groups are acetyl, benzyloxycarbonyl or trifluoroacetyl, most preferably acetyl.

Suitable metabolism inhibiting groups for the peptide carboxyl terminus include: carboxamide, tert-butyl ester, benzyl ester, cyclohexyl ester, amino alcohol or a polyethyleneglycol (PEG) building block. A suitable $M^{IG}$ group for the carboxy terminal amino acid residue of the BTM peptide is where the terminal amine of the amino acid residue is N-alkylated with a $C_{1-4}$ alkyl group, preferably a methyl group. Preferred such $M^{IG}$ groups are carboxamide or PEG, most preferred such groups are carboxamide.

In the method of the first aspect, the linker group $L^1$ is preferably present. The linker groups $L^2$ and $L^3$ are optional, but are preferably absent. When the linker group comprises a $C_{3-12}$ heteroarylene group, the heteroatoms are suitably chosen from N, O and S; preferably N and O.

When $L^1$ comprises a peptide chain of 1 to 10 amino acid residues, the amino acid residues are preferably chosen from glycine, lysine, arginine, aspartic acid, glutamic acid or serine. When $L^1$ comprises a PEG moiety, it preferably comprises units derived from oligomerisation of the monodisperse PEG-like structures of Formulae Bio1 or Bio2:

17-amino-5-oxo-6-aza-3,9,12,15-tetraoxaheptadecanoic acid of Formula Bio1 wherein p is an integer from 1 to 10. Alternatively, a PEG-like structure based on a propionic acid derivative of Formula Bio2 can be used:

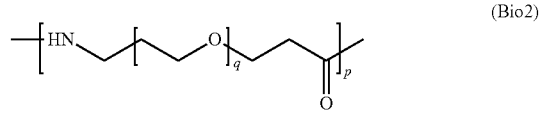

(Bio2)

where p is as defined for Formula Bio1 and q is an integer from 3 to 15. In Formula Bio2, p is preferably 1 or 2, and q is preferably 5 to 12.

When the linker group does not comprise PEG or a peptide chain, preferred $L^1$ groups have a backbone chain of linked atoms which make up the -(A)$_m$- moiety of 2 to 10 atoms, most preferably 2 to 5 atoms, with 2 or 3 atoms being especially preferred.

BTM peptides which are not commercially available can be synthesised by solid phase peptide synthesis as described in P. Lloyd-Williams, F. Albericio and E. Girald; *Chemical Approaches to the Synthesis of Peptides and Proteins*, CRC Press, 1997.

In the method of the first aspect, the compound of Formula (I) may optionally be generated by deprotection of a compound of Formula (Ia):

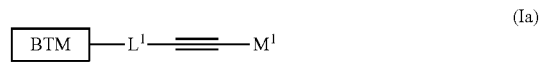

(Ia)

wherein $M^1$ is an alkyne-protecting group.

Preferred aspects of $L^1$ in Formula (Ia), are as described for Formula (I).

The method of the present invention tolerates a wide range of functional groups in the BTM. However, when the BTM comprises free thiol groups (e.g. a reduced cysteine-containing peptide), such thiol groups are preferably protected before the reaction of the first aspect is carried out. Similarly, any chelating functionalities or groups which coordinate well to copper(I) may require protection.

By the term "protecting group" is meant a group which inhibits or suppresses undesirable chemical reactions, but which is designed to be sufficiently reactive that it may be

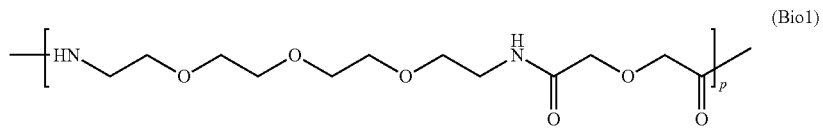

(Bio1)

cleaved from the functional group in question under mild enough conditions that do not modify the rest of the molecule. After deprotection the desired product is obtained. Suitable protecting groups are described in 'Protective Groups in Organic Synthesis', Theodora W. Greene and Peter G. M. Wuts, $4^{th}$ edition (John Wiley & Sons, 2007). Alkyne protecting groups are described at Chapter 8, pages 927-933 therein, and include: an trialkylsilyl group where each alkyl group is independently $C_{1-4}$ alkyl; an aryldialkylsilyl group where the aryl group is preferably benzyl or biphenyl and the alkyl groups are each independently $C_{1-4}$ alkyl; hydroxymethyl or 2-(2-hydroxypropyl). A preferred such alkyne protecting group is trimethylsilyl. The protected alkynes of Formula (Ia) have the advantage that the desired alkyne of Formula (I) can be generated in a controlled manner, so that the efficiency of the click cycloaddition reaction with the compound of Formula (IIa) or (IIb) can be maximised.

The click radioiodination method of the first aspect may be effected in a suitable solvent, for example acetonitrile, a $C_{1-4}$ alkylalcohol, dimethylformamide, tetrahydrofuran, or dimethylsulfoxide, or aqueous mixtures of any thereof, or in water. Aqueous buffers can be used in the pH range of 4-8, more preferably 5-7. The reaction temperature is preferably 5 to 100° C., more preferably at 75 to 85° C., most preferably at ambient temperature (typically 15-37° C.). The click cycloaddition may optionally be carried out in the presence of an organic base, as is described by Meldal and Tornoe [Chem. Rev. 108, 2952, Table 1 (2008)].

A preferred click cycloaddition catalyst comprises Cu(I). The Cu(I) catalyst is present in an amount sufficient for the reaction to progress, typically either in a catalytic amount or in excess, such as 0.02 to 1.5 molar equivalents relative to the compound of Formula (IIa) or (IIb). Suitable Cu(I) catalysts include Cu(I) salts such as CuI or [Cu(NCCH$_3$)$_4$][PF$_6$], but advantageously Cu(II) salts such as copper (II) sulfate may be used in the presence of a reducing agent to generate Cu(I) in situ. Suitable reducing agents include: ascorbic acid or a salt thereof for example sodium ascorbate, hydroquinone, metallic copper, glutathione, cysteine, $Fe^{2+}$, or $Co^{2+}$. Cu(I) is also intrinsically present on the surface of elemental copper particles, thus elemental copper, for example in the form of powder or granules may also be used as catalyst. Elemental copper, with a controlled particle size is a preferred source of the Cu(I) catalyst. A more preferred such catalyst is elemental copper as copper powder, having a particle size in the range 0.001 to 1 mm, preferably 0.1 mm to 0.7 mm, more preferably around 0.4 mm. Alternatively, coiled copper wire can be used with a diameter in the range of 0.01 to 1.0 mm, preferably 0.05 to 0.5 mm, and more preferably with a diameter of 0.1 mm. The Cu(I) catalyst may optionally be used in the presence of bathophenanthroline, which is used to stabilise Cu(I) in click chemistry.

The non-radioactive precursor compounds of Formula (I), wherein the BTM is a peptide or protein may be prepared by standard methods of peptide synthesis, for example, solid-phase peptide synthesis, for example, as described in Atherton, E. and Sheppard, R. C.; "Solid Phase Synthesis"; IRL Press: Oxford, 1989. Incorporation of the alkyne group in a compound of Formula (Ia) or (Ib) may be achieved by reaction of the N or C-terminus of the peptide or with some other functional group contained within the peptide sequence, modification of which does not affect the binding characteristics of the vector. The alkyne group is preferably introduced by formation of a stable amide bond, for example formed by reaction of a peptide amine function with an activated acid or alternatively reaction of a peptide acid function with an amine function and introduced either during or following the peptide synthesis. Methods for incorporation of an alkyne group into vectors such as cells, viruses, bacteria may be found in H. C. Kolb and K. B. Sharpless, Drug Discovery Today, Vol 8 (24), 1128 December 2003 and the references therein. Suitable bifunctional intermediates useful for incorporation of the alkyne group in a compound of Formula (I) include:

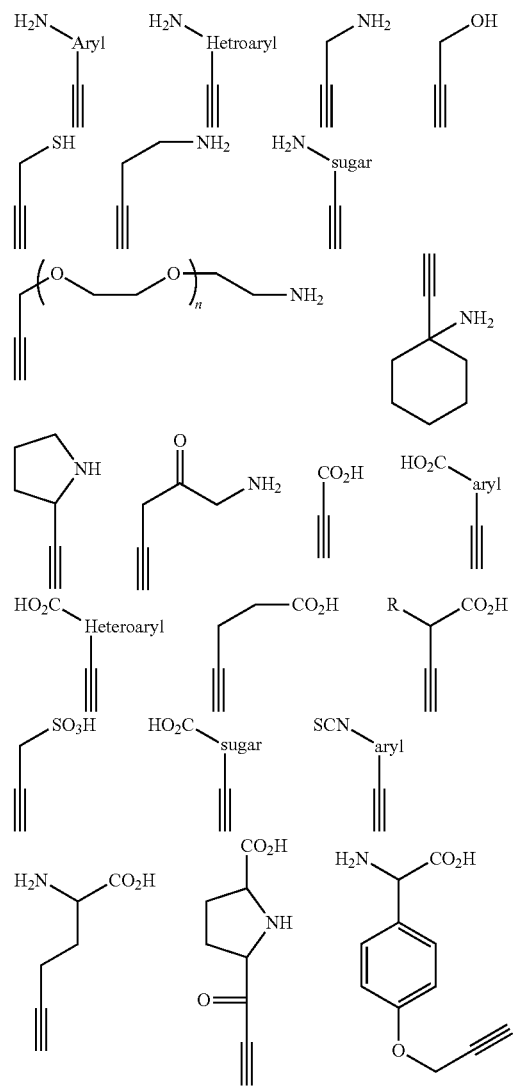

where $L^1$ and preferred embodiments thereof are as defined above. In the above formulae, $L^1$ is suitably present. In the azide-functionalised amino acid, however, the azide functional group may optionally be attached directly to the side chain of the amino acid without any linker group. Alkyne precursors of this type are described by Glaser and Arstad [Bioconj. Chem., 18, 989-993 (2007)]. The same authors also describe methods of introducing alkyne groups into peptides.

Further approaches to functionalising BTMs with alkyne groups are described by Nwe et al [Cancer Biother. Radiopharm., 24(3), 289-302 (2009)]. Smith et al provide the synthesis of alkyne-functionalised isatin precursors, where the isatin compound is specific for caspase-3 or caspase-7 [J. Med. Chem., 51(24), 8057-8067 (2008)]. De Graaf et al [Bioconj. Chem., 20(7), 1281-1295 (2009)] describe non-natural amino acids having alkyne side chains and their site-specific incorporation in peptides or proteins for subsequent click conjugation. Example 7 (below) provides a bifunctional alkyne-maleimide, which can be used to conjugate with the thiol group of a thiol-containing BTM to introduce an alkyne group suitable for subsequent click cycloaddition.

Radioiodinated azides of Formula (IIa) can be synthesized by the method of Bercovici et al [Biochemistry, 17(8), 1484-1489 (1978)]. 1-Azido-4-[$^{125}$I]iodobenzene (i.e. $Y^1$ is a 1,4-phenylene group) can be obtained by the method of Booth et al (for I*=$^{125}$I) as follows [Biochem. J., 179, 397-405 (1979)]:

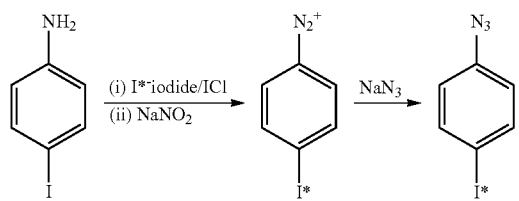

An additional option is to start from aniline, and radioiodinate that directly (since the para position is the most activated), using electrophilic substitution and a suitable oxidant. Aniline can be iodinated in this way, followed by diazotisation to give the diazonium intermediate shown above. Alternatively, a trialkyltin precursor could be used to ensure regiospecificity.

The nitrile oxides of Formula (IIb) can be obtained by the methods described by Ku et at [Org. Lett., 3(26), 4185-4187 (2001)], and references therein. Thus, they are typically generated in situ by treatment of an alpha-halo aldoxime with an organic base such as triethylamine. A preferred method of generation, as well as conditions for the subsequent click cyclisation to the desired isoxazole are described by Hansen et al [J. Org. Chem., 70(19), 7761-7764 (2005)]. Hansen et al generate the desired alpha-halo aldoxime in situ by reaction of the corresponding aldehyde with chloramine-T trihydrate, and then dechlorinating this with sodium hydroxide. The corresponding aldoxime is prepared by reacting the corresponding aldehyde with hydroxylamine hydrochloride at pH 9-10. See also K. B. G. Torsell "Nitrile Oxides, Nitrones and Nitronates in Organic Synthesis" [VCH, New York (1988)].

Due to the instability of the nitrile oxide group, these are most suitably introduced into a compound of Formula (IIa) in situ, for example from the corresponding aldehyde or masked nitrile oxide, such as a cyclic sulfite ester.

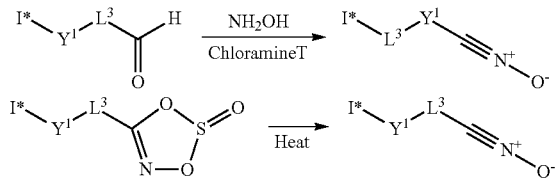

In one embodiment, there is provided a compound of Formula (IIa) wherein $Y^1$ is 1,4-phenylene; such compound being readily prepared according to Example 1 (below).

The compounds of Formula (IIa) or (IIb) are preferably generated from non-radioactive precursors as follows:
reaction of a precursor of either Formula (IVa) or Formula (IVb) respectively:

$R^a{}_3Sn—Y^1-L^2-N_3$ (IVa)

$KF_3B—Y^1-L^3C≡N^+—O^-$ (IVb)

wherein $Y^1$, $L^2$ and $L^3$ and preferred embodiments thereof are as defined above, and each $R^a$ is independently $C_{1-4}$ alkyl;
with a supply of radioactive iodide ion in the presence of an oxidising agent, to give the compound of Formula (IIa) or (IIb) respectively.

The precursor of Formula (IVa) or (IVb) is non-radioactive. Organotin intermediates are described by Ali et al [Synthesis, 423-445 (1996)]. Suitable oxidising agents are described by Bolton [J. Lab. Comp. Radiopharm., 45, 485-528 (2002)]. Preferred oxidising agents are peracetic acid at pH ca. 4, and hydrogen peroxide/aqueous HCl at pH ca. 1. The synthesis of potassium alkynyltrifluoroborate precursors is described by Kabalka et al [J. Lab. Comp. Radiopharm., 48, 359-362 (2005) and J. Lab. Comp. Radiopharm., 49, 11-15 (2006)]. The potassium alkynyltrifluoroborate precursors are stated to be crystalline solids, which are stable to both air and water.

The present invention provides a more chemoselective approach to radioiodination. The ligation reaction occurs at a predetermined site in the BTM, giving only one possible product. This methodology is therefore chemoselective. Additionally, both alkyne and azide functionalities are stable under most reaction conditions and are unreactive with most common peptide functionalities—thus minimising the protection and deprotection steps required during the radiolabelling synthesis. Furthermore, the triazole and isoxazole rings formed during the labelling reaction do not hydrolyse and are highly stable to oxidation and reduction, meaning that the labelled BTM has high in vivo stability. The triazole ring is also comparable to an amide in size and polarity such that the labelled peptides or proteins are good mimics for their natural counterparts—the triazole ring in particular is a known amide mimetic group or bioisostere.

The method of the first aspect is preferably carried out in an aseptic manner, such that the product of Formula (IIIa) or (IIIb) is obtained as a radiopharmaceutical composition. Further description of the radiopharmaceutical composition is given in the fourth aspect (below). Thus, the method is carried out under aseptic manufacture conditions to give the desired sterile, non-pyrogenic radiopharmaceutical product. It is preferred therefore that the key components, especially any parts of the apparatus which come into contact with the product of Formula (IIIa) or (IIIb) (eg. vials and transfer tubing) are sterile. The components and reagents can be sterilised by methods known in the art, including: sterile filtration, terminal sterilisation using e.g. gamma-irradiation, autoclaving, dry heat or chemical treatment (e.g. with ethylene oxide). It is preferred to sterilise the non-radioactive components in advance, so that the minimum number of manipulations need to be carried out on the radioiodinated radiopharmaceutical product. As a precaution, however, it is preferred to include at least a final sterile filtration step.

The compounds of Formulae (I), (IIa) and/or (IIb), plus click cycloaddition catalyst and other such reagents and solvents are each supplied in suitable vials or vessels which comprise a sealed container which permits maintenance of sterile integrity and/or radioactive safety, plus optionally an inert headspace gas (eg. nitrogen or argon), whilst permitting addition and withdrawal of solutions by syringe or cannula. A preferred such container is a septum-sealed vial, wherein the gas-tight closure is crimped on with an overseal (typically of aluminium). The closure is suitable for single or multiple puncturing with a hypodermic needle (e.g. a crimped-on septum seal closure) whilst maintaining sterile integrity. Such containers have the additional advantage that the closure can withstand vacuum if desired (eg. to change the headspace gas or degas solutions), and withstand pressure changes such as reductions in pressure without permitting ingress of external atmospheric gases, such as oxygen or water vapour. The reaction vessel is suitably chosen from such containers, and preferred embodiments thereof. The reaction vessel is preferably made of a biocompatible plastic (eg. PEEK).

The method of the first aspect is preferably carried out using an automated synthesizer apparatus. By the term "automated synthesizer" is meant an automated module based on the principle of unit operations as described by Satyamurthy et al [Clin. Positr. Imag., 2(5), 233-253 (1999)]. The term 'unit operations' means that complex processes are reduced to a series of simple operations or reactions, which can be applied to a range of materials. Such automated synthesizers are preferred for the method of the present invention especially when a radiopharmaceutical product is desired. They are commercially available from a range of suppliers [Satyamurthy et al, above], including: GE Healthcare; CTI Inc; Ion Beam Applications S.A. (Chemin du Cyclotron 3, B-1348 Louvain-La-Neuve, Belgium); Raytest (Germany) and Bioscan (USA).

Commercial automated synthesizers also provide suitable containers for the liquid radioactive waste generated as a result of the radiopharmaceutical preparation. Automated synthesizers are not typically provided with radiation shielding, since they are designed to be employed in a suitably configured radioactive work cell. The radioactive work cell provides suitable radiation shielding to protect the operator from potential radiation dose, as well as ventilation to remove chemical and/or radioactive vapours. The automated synthesizer preferably comprises a 'cassette' as described in the seventh aspect (below).

In a second aspect, the present invention provides a compound of Formula (IIIa) or (IIIb):

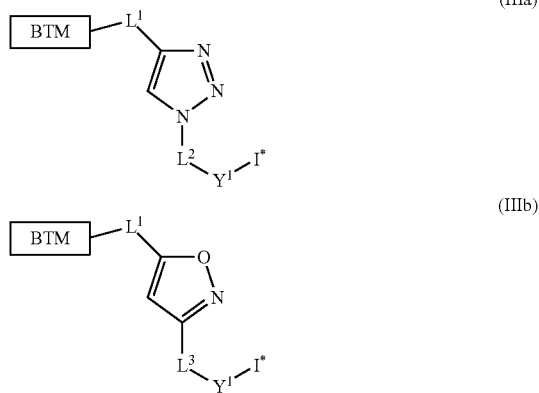

where: $L^1$, $L^2$, $L^3$, $Y^1$, BTM and I* including preferred aspects thereof are as defined in the first aspect (above).

Preferably, the compound of the second aspect is of Formula (IIIa). In the compounds of Formula (IIIa) and (IIIb), the linker groups ($L^2$ and $L^3$ respectively) are preferably absent. The present invention also provides a compound of Formula (IIIa) or (IIIb) as defined in the second aspect for medical use—preferably the compound of Formula (IIIa).

In a third aspect, the present invention provides a compound of Formula (IIaa) or (IIbb), useful in the method of the first aspect:

where I* and $Y^1$ including preferred aspects thereof, are as defined above. The compounds of Formula (IIaa) or (IIbb) may preferably be supplied as pharmaceutical compositions, together with a biocompatible carrier medium. Such compositions, including preferred aspects thereof, are as defined in the fourth aspect (below).

In a fourth aspect, the present invention provides a radiopharmaceutical composition comprising an effective amount of a compound of Formula (IIIa) or (IIIb) according to the second aspect, together with a biocompatible carrier medium. Preferred embodiments of I*, $L^1$ and BTM are as defined in the first aspect (above). The compound of the third aspect is also preferably a triazole of Formula (IIIa).

The "biocompatible carrier medium" comprises one or more pharmaceutically acceptable adjuvants, excipients or diluents. It is preferably a fluid, especially a liquid, in which the compound of Formula (IIIa) or (IIIb) is suspended or dissolved, such that the composition is physiologically tolerable, i.e. can be administered to the mammalian body without toxicity or undue discomfort. The biocompatible carrier medium is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (eg. salts of plasma cations with biocompatible counterions), sugars (e.g. glucose or sucrose), sugar alcohols (eg. sorbitol or mannitol), glycols (eg. glycerol), or other non-ionic polyol materials (eg. polyethyleneglycols, propylene glycols and the like). The biocompatible carrier medium may also comprise biocompatible organic solvents such as ethanol. Such organic solvents are useful to solubilise more lipophilic compounds or formulations. Preferably the biocompatible carrier medium is pyrogen-free water for injection, isotonic saline or an aqueous ethanol solution. The pH of the biocompatible carrier medium for intravenous injection is suitably in the range 4.0 to 10.5.

In a fifth aspect, the present invention provides the use of a compound according to the second or fourth aspects, for the manufacture of a radiopharmaceutical for use in a method of in vivo imaging or in vivo radiotherapy. Preferably, the use is in a method of in vivo imaging, more preferably of the intact mammalian (especially human) body, most preferably such imaging via PET or SPECT. Preferably, the use of the fifth aspect comprise the Compounds of Formula (IIIa) or Formula (IIIb), more preferably Formula (IIIa).

In a sixth aspect, the present invention provides the use of an automated synthesizer apparatus to carry out the method of the first aspect.

The automated synthesizer apparatus and preferred embodiments thereof are as described in the first aspect (above).

In a seventh aspect, the present invention provides a single use, sterile cassette suitable for use in the automated synthesizer of the preferred embodiment of the first aspects, said cassette comprising the non-radioactive reagents necessary to carry out the method of the first aspect in sterile, apyrogenic form.

Preferred embodiments of the above methods for use in the seventh aspect are as described in the first aspect.

By the term "cassette" is meant a piece of apparatus designed to fit removably and interchangeably onto an automated synthesizer apparatus (as defined below), in such a way that mechanical movement of moving parts of the synthesizer controls the operation of the cassette from outside the cassette, i.e. externally. Suitable cassettes comprise a linear array of valves, each linked to a port where reagents or vials can be attached, by either needle puncture of an inverted septum-sealed vial, or by gas-tight, marrying joints. Each valve has a male-female joint which interfaces with a corresponding moving arm of the automated synthesizer. External rotation of the arm thus controls the opening or closing of the valve when the cassette is attached to the automated synthesizer. Additional moving parts of the automated synthesizer are designed to clip onto syringe plunger tips, and thus raise or depress syringe barrels.

The cassette is versatile, typically having several positions where reagents can be attached, and several suitable for attachment of syringe vials of reagents or chromatography cartridges (eg. SPE). The cassette always comprises a reaction vessel. Such reaction vessels are preferably 1 to 10 $cm^3$, most preferably 2 to 5 $cm^3$ in volume and are configured such that 3 or more ports of the cassette are connected thereto, to permit transfer of reagents or solvents from various ports on the cassette. Preferably the cassette has 15 to 40 valves in a linear array, most preferably 20 to 30, with 25 being especially preferred. The valves of the cassette are preferably each identical, and most preferably are 3-way valves. The cassettes of the present invention are designed to be suitable for radiopharmaceutical manufacture and are therefore manufactured from materials which are of pharmaceutical grade and ideally also are resistant to radiolysis.

Preferred automated synthesizers of the present invention are those which comprise a disposable or single use cassette which comprises all the reagents, reaction vessels and apparatus necessary to carry out the preparation of a given batch of radioiodinated radiopharmaceutical. The cassette means that the automated synthesizer has the flexibility to be capable of making a variety of different radioiodine-labelled radiopharmaceuticals with minimal risk of cross-contamination, by simply changing the cassette. The cassette approach also has the advantages of: simplified set-up hence reduced risk of operator error; improved GMP (Good Manufacturing Practice) compliance; multi-tracer capability; rapid change between production runs; pre-run automated diagnostic checking of the cassette and reagents; automated barcode cross-check of chemical reagents vs the synthesis to be carried out; reagent traceability; single-use and hence no risk of cross-contamination, tamper and abuse resistance.

In an eighth aspect, the present invention provides method of generating an image of a human or animal body comprising administering a compound according to the second aspect, or the radiopharmaceutical composition according to the third aspect and generating an image of at least a part of said body to which said compound or composition has distributed using PET or SPECT.

In a further aspect, the present invention provides a method of monitoring the effect of treatment of a human or animal body with a drug, said method comprising administering to said body a compound according to the second aspect, or the composition according to the third aspect, and detecting the uptake of said compound or composition in at least a part of said body to which said compound or composition has distributed using PET or SPECT.

The administration and detection of this final aspect are preferably effected before and after treatment with said drug, so that the effect of the drug treatment on the human or animal patient can be determined. Where the drug treatment involves a course of therapy, the imaging can also be carried out during the treatment.

The invention is illustrated by the following Examples. Example 1 provides the synthesis of authentic samples of the non-radioactive (iodine isotope $^{127}$I) iodinated triazole analogues Compound 1 and Compound 2. Example 2 provides the synthesis of $^{123}$I-4-iodophenyl azide, an important precursor for the click radiolabelling chemistry of the present invention. Example 3 provides the synthesis of a radioiodinated triazole ring using the click cycloaddition method of the present claims (Compound 1A), using two alternative click cycloaddition catalysts. The synthesis can be carried out at room temperature, demonstrating suitability for labelling BTMs under mild conditions. Example 4 provides a further synthesis forming a radioiodinated triazole ring (Compound 2A). Example 5 provides the synthesis of authentic samples of the non-radioactive (iodine isotope $^{127}$I) iodinated isoxazole analogue Compound 3. Example 6 provides the synthesis of a radioiodinated isoxazole ring using the click cycloaddition method of the present claims (Compound 3A). Example 7 provides the synthesis of a bifunctional alkyne-maleimide, suitable for covalent conjugation with the thiol groups of a BTM to introduce alkyne groups.

ABBREVIATIONS

DCM: dichloromethane,
DMF: dimethylformamide,
HPLC: high performance liquid chromatography
MeCN: acetonitrile
PAA: peracetic acid,
RCP: radiochemical purity
RT: room temperature.
$t_R$: retention time.
Compounds of the Invention.

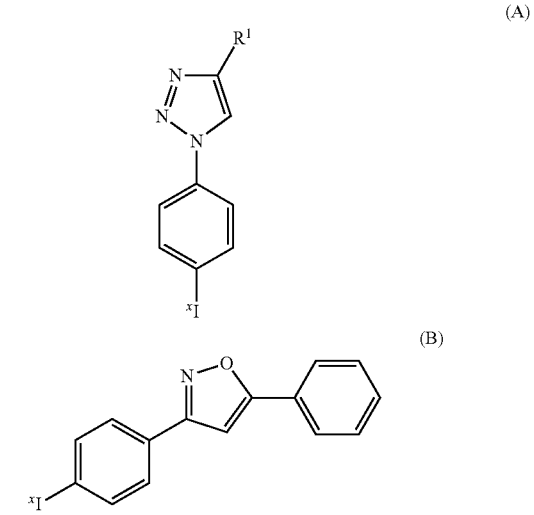

| Compound | Formula | $R^1$ | x |
|---|---|---|---|
| 1 | A | —(CO(NH)benzyl | 127 |
| 1A | A | —(CO(NH)benzyl | 123 |
| 2 | A | -phenyl | 127 |
| 2A | A | -phenyl | 123 |
| 3 | B | not applicable | 127 |
| 3A | B | not applicable | 123 |

Example 1

Preparation of N-Benzyl 1-(4-iodophenyl)-1,2,3-triazolyl-4-carboxamide (Compound 1) and 1-(4-Iodophenyl)-4-phenyl-1,2,3-triazole (Compound 2)

Step (a): Preparation of N-hydroxysuccinimidyl propiolate

A solution of propiolic acid (2.1 g, 30 mmol) and N-hydroxysuccinimide (3.45 g, 30 mmol) in 1,2-dimethoxyethane (40 mL) was treated with 1,3-dicyclohexylcarbodiimide (6.19 g, 30 mmol) in 1,2-dimethoxyethane (35 mL) by dropwise addition at ambient temperature. The mixture became cloudy during the course of the addition. The mixture was allowed to stir overnight and the solid was filtered off and the filtrate was evaporated to give 5.1 g of a pale brown solid.

$^1$H NMR (300 MHz, CDCl$_3$) $\delta_H$ 2.83 (4H, s, 2×C$\underline{H}_2$), and 3.38 (1H, s, C$\underline{H}$).

Step (b): Preparation of N-benzyl propynamide

A solution of N-hydroxysuccinimidyl propiolate (5.1 g, 30 mmol) in dichloromethane (100 mL) was cooled with an ice bath for 30 minutes. Benzylamine (2.89 g, 27 mmol, 2.95 mL) was added dropwise over 2-3 minutes. The mixture was allowed to warm to ambient temperature by allowing the ice bath to melt. During this time a precipitate formed in the reaction. The mixture was then stirred overnight. The solid was filtered off and the filtrate evaporated to give 5.4 g of a dark yellow oil. Around 2.2 g of material was filtered through a pad of silica gel eluting with dichloromethane. This resulted in 1.3 g (27%) of a pale yellow solid. $^1$H NMR showed that the material was consistent with the desired material—purity between 80 and 90%.

$^1$H NMR (CDCl$_3$, 300 MHz) $\delta_H$ 2.80 (1H, s, CC$\underline{H}$), 4.48 (2H, d, J=2.7 Hz, C$\underline{H}_2$), 6.19 (1H, br s, N$\underline{H}$), and 7.33 (5H, m, 5×Ar$\underline{H}$

Step (c): Preparation of 1-(4-Iodophenyl)-4-phenyl-1,2,3-triazole (Compound 2) and N-Benzyl 1-(4-iodophenyl)-1,2,3-triazolyl-4-carboxamide (Compound 1)

4-Iodophenyl boronic acid (496 mg, 2 mmol) was added to a stirred, dark yellow solution of copper sulfate (50 mg, 0.2 mmol) and sodium azide (1.56 mg, 2.4 mmol) in methanol (6 mL). The mixture was stirred vigorously for 24 hours. Over the reaction time, the dark yellow solution became a yellowy-green fine suspension. Water (7 mL) was added causing the mixture to become a green milky suspension. This was divided into two portions. Each suspension was treated with sodium ascorbate (99 mg) and one treated with (A) N-benzyl propynamide (159 mg), and the other (B) with phenylacetylene (102 mg, 110 µL). The two mixtures were stirred vigorously at ambient temperature for 6 hours. The mixtures changed from green milky suspensions to yellow milky suspensions in a few minutes and then separated out to give powdery solids suspended in the water/methanol mix. The solids were filtered off, washed with water and dried in vacuo overnight to give the two desired materials:

A) Compound 1 (140 mg, 35%), as an off-white powder. $^1$H NMR (300 MHz, D$_6$-DMSO) 4.49 (2H, d, J=6.4 Hz, C$\underline{H}_2$), 7.20-7.35 (5H, m, CH$_2$C$_6$$\underline{H}_5$), 7.80 (2H, d, J=8.7 Hz, 1-(2,6-Ar$\underline{H}$)), 7.98 (2H, d, J=8.7 Hz, 1-(3,5-Ar$\underline{H}$)), 9.26 (1H, t, J=6.4 Hz, N$\underline{H}$), and 9.32 (1H, s, 5-Ar$\underline{H}$).

m/z calc'd for C$_{16}$H$_{13}$IN$_4$O 404.0. found 404.5B) Compound 2 (190 mg, 55%) as a pale yellow powder. $^1$H NMR (300 MHz, D$_6$-DMSO) 7.39 (1H, t, J=7.4 Hz, 4-(4-Ar$\underline{H}$)), 7.51 (2H, t, J=7.4 Hz, 4-(3,5-Ar$\underline{H}$)), 7.79 (2H, d, J=8.4 Hz, 1-(2,6-Ar$\underline{H}$)), 7.94 (2H, d, J=7.4 Hz, 4-(2,6-Ar$\underline{H}$)), 8.02 (2H, d, J=8.4 Hz, 1-(3,5-Ar$\underline{H}$)), and 9.35 (1H, s, 5-Ar$\underline{H}$).

m/z calc'd for C$_{14}$H$_{10}$IN$_3$ 347.0. found 347.6.

Example 2

Preparation of [$^{123}$I]-4-iodo phenyl azide

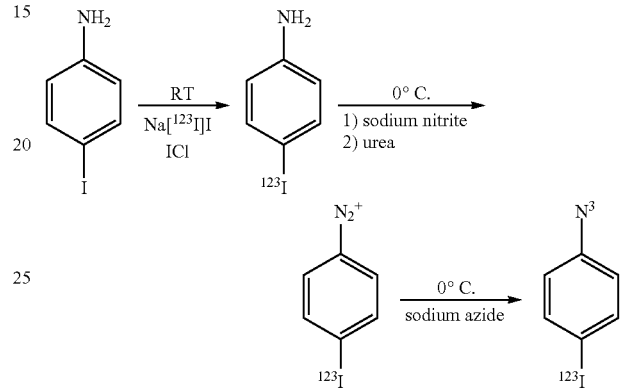

This is based on the method of Booth et al [Biochem. J., 179, 397-405 (1979)]. The iodine monochloride (ICl) reagent was prepared as follows: into 10 mL 1M hydrochloric acid was dissolved sodium chloride (1.168 g), potassium iodide (20.8 mg) and potassium iodate (13.4 mg). 1.0 mL of this orange solution was then transferred to a scintillation vial containing 1.2 mL of a 3.3 mM solution of potassium iodate (7.06 mg dissolved in 10 mL water), 0.9 mL 37% hydrochloric acid and 3.7 mL 2M sodium chloride. The pale yellow/orange solution was stored at −4° C.

To ~5 µL sodium [$^{123}$I] iodide (137 MBq) was added aqueous sodium hydroxide (20 µL 0.01M), 4-iodoaniline (100 µg, 4.6×10$^{-7}$ moles) dissolved in 0.5M hydrochloric acid (0.1 mL) and iodine monochloride reagent (20 µL). The reaction mixture was incubated at room temperature for 20 minutes. HPLC analysis showed 4-[$^{123}$I] iodoaniline (t$_R$ 5 minutes, system A) with an RCP of >90%.

To crude [$^{123}$I]-4-iodoaniline cooled in an ice bath, was added sodium nitrite (20 µL, 9.4×10$^{-7}$ moles, 1.6 mg, dissolved in 0.5 mL water). After 20 minutes, was added urea (20 µL, 1.67×10$^{-6}$ moles, 2.5 mg, dissolved in 0.5 mL water) and sodium azide (15 µL, 1.42×10$^{-6}$ moles, 3.12 mg dissolved in 0.5 mL water). After 10 minutes, the ice was removed and the cloudy solution transferred to a scintillation vial. The reaction vial was rinsed with 2×0.5 mL acetonitrile and transferred to the same scintillation vial. The resulting clear solution was diluted with 10 mL water, loaded onto a tC18-light (pre-treated with 2.5 mL MeCN and 5 mL water) and eluted in 0.6 mL acetonitrile to afford the purified product, 4-[$^{123}$I] iodophenylazide in 55% yield (non decay corrected) with an RCP of >90% (HPLC t$_R$ 13 minutes, system A).

HPLC System A (A=0.1% TFA in water; B=0.1% TFA in acetonitrile).

Column C18 (2) phenonenex Luna, 150×4.6 mm, 5 micron.

| | | Time (min) | | | | |
|---|---|---|---|---|---|---|
| | | 0 | 1 | 20 | 22 | 22.5 | 25 |
| Gradient | % B | 50 | 50 | 95 | 95 | 50 | 50 |

Example 3

Preparation of [$^{123}$I]-N-Benzyl 1-(4-iodophenyl)-1,2,3-triazolyl-4-carboxamide (Compound 1A)

Option 1: Using Copper Powder.

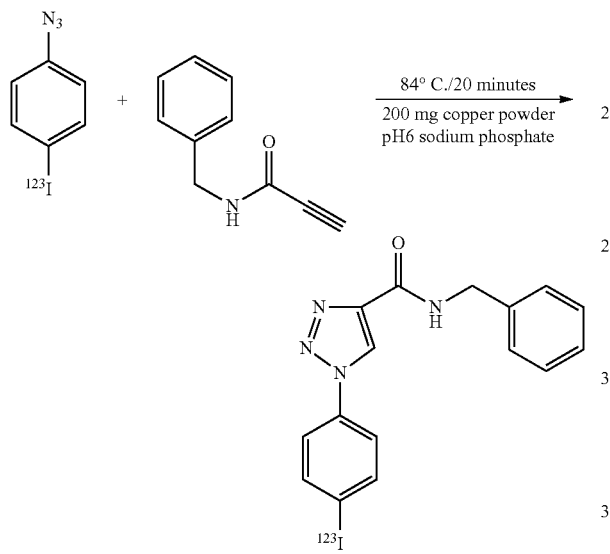

This method is based on Glaser et al [Bioconj. Chem., 18(3), 989-993 (2007)].

To copper powder (~40 mesh, 200 mg) in a wheaton vial was added, sodium phosphate buffer (200 μL, pH 6, 50 mM), N-benzylpropynamide (1.0 mg dissolved in 0.1 mL DMF, $6.3 \times 10^{-6}$ moles) and 4-[$^{123}$I] iodophenylazide in 0.2 mL MeCN (22 MBq). The reaction was heated at 84° C. for 20 minutes. After cooling, a 10 μL sample was analysed by HPLC indicating the desired product with an RCP of 84% (HPLC $t_R$-9 minutes, system A, Example 2). The crude preparation was diluted with 0.5 mL 0.1% TFA in acetonitrile and 0.6 mL 0.1% TFA in water and the desired product isolated by HPLC (System A, Example 2) in 58% yield (non decay corrected) with an RCP of 100%. Co-elution of the purified product with authentic Compound 1 (Example 1) was observed.

The reaction can also be carried out at room temperature, when a 17% yield was obtained, with an RCP of 100%.

Option 2: Using Copper(II) Sulfate and Sodium Ascorbate.

To a solution of copper (II) sulfate (50 μL, 0.045M solution) in a wheaton vial was added, sodium ascorbate solution (50 μL, 0.15 M solution), sodium phosphate buffer (100 μL, pH 6, 50 mM), N-benzylpropynamide (1.0 mg dissolved in 0.1 mL DMF, $6.3 \times 10^{-6}$ moles) and 0.2 mL 4-[$^{123}$I] iodophenylazide in MeCN (22 MBq). The reaction was heated at 84° C. for 20 minutes. After cooling, the crude preparation was diluted with 0.5 mL 0.1% TFA in acetonitrile and 0.6 mL 0.1% TFA in water and the desired product isolated by HPLC (System A, Example 2) in 56% yield (non decay corrected) with an RCP of 100%. Co-elution of the purified product with authentic Compound 1 (Example 1) was observed.

Example 4

Preparation of [$^{123}$I]-1-(4-iodophenyl)-4-phenyl-1,2,3-triazole (Compound 2A)

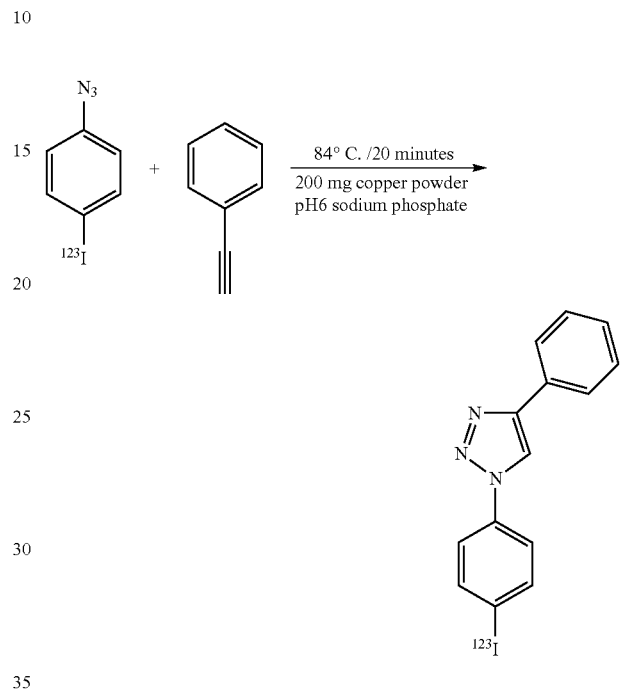

This method is based on Glaser et al [Bioconj. Chem., 18(3), 989-993 (2007)]. To copper powder (~40 mesh, 200 mg) in a wheaton vial was added, sodium phosphate buffer (200 μL, pH 6, 50 mM), phenylacetylene (0.64 mg dissolved in 0.1 mL DMF, $6.3 \times 10^{-6}$ moles) and finally, 0.2 mL 4-[$^{123}$I] iodophenylazide in MeCN (28 MBq). The reaction was heated at 84° C. for 20 minutes. After cooling, a 10 μL sample was analysed by HPLC indicating the desired product with an RCP of 85% (HPLC tR 22.5 minutes, system B). The crude preparation was diluted with 0.4 mL 0.1% TFA in acetonitrile and 0.7 mL 0.1% TFA in water and the desired product isolated by HPLC (system B) in 48% yield (non decay corrected) with an RCP of 100%. Co-elution of the purified product with authentic Compound 2 (Example 1) was observed.

HPLC System B

A=0.1% TFA in water

B=0.1% TFA in acetonitrile

Column C18 (2) phenonenex Luna, 150×4.6 mm, 5 micron

| | | Time (min) | | | | |
|---|---|---|---|---|---|---|
| | | 0 | 25 | 27 | 29.5 | 30.5 | 37 |
| Gradient | % B | 45 | 45 | 95 | 95 | 45 | 45 |

Example 5

Synthesis of 3-(4-Iodophenyl)-5-phenylioxazole (Compound 3)

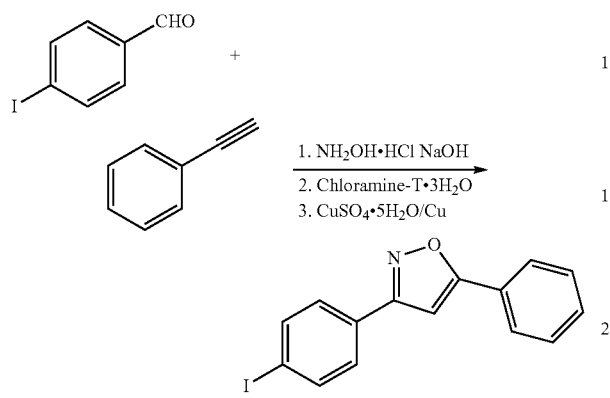

See J. Org. Chem. 70, 7761-7764 (2005).

To a solution of hydroxylamine hydrochloride (79 mg, 1.13 mmol) in t-butanol (8 mL) and water (8 mL) was added 4-iodobenzaldehyde (250 mg, 1.07 mmol) and then sodium hydroxide (45 mg, 1.05 mmol) and the mixture was stirred at ambient temperature for 30 mins. Then was added chloramine-T trihydrate (318 mg, 1.13 mmol) in one portion, followed by copper sulfate (7.5 mg, 0.03 mmol) and copper turnings (ca. 20 mg), ethynyl benzene (115 mg, 1.13 mmol, 120 μL) was added. The pH was adjusted to ~6 by addition of a few drops of 2N HCl and was stirred for 18 hours at ambient temperature. The reaction mixture was poured into ice/water (30 mL), dilute ammonium hydroxide solution (10 mL) was added and the product was collected by filtration. The product was re-dissolved in DCM and passed through a plug of silica gel eluting with 20% ethyl acetate: petroleum ether (75 mL) to afford an impure off-white solid. The material was purified further by silica gel chromatography eluting with 5-10% EtOAc in petrol. This yielded a white solid (10 mg, 3%). $^1$H NMR (300 MHz, CDCl$_3$): δH 6.80 (1H, s), 7.47 (3H, m), 7.60 (2H, m), and 7.82 (4H, m); $^{13}$C NMR (75 MHz, CDCl$_3$): δH 96.4, 97.2, 125.9, 127.3, 128.4, 128.6, 129.0, 130.4, 162.2, and 170.7.

Example 6

Preparation of [$^{123}$I]-3-(4-iodophenyl)-5-phenylisoxazole (Compound 3A)

Step (a): Preparation of [$^{123}$I] 4-iodobenzaldehyde

To 5.2 μL sodium [$^{123}$I] iodide (138.1 MBq) was added, ammonium acetate buffer (100 μL, pH 4, 0.2M), sodium [$^{127}$I] iodide (51 μL, 10 mM solution in 0.01M sodium hydroxide, $5.1 \times 10^{-7}$ moles), peracetic acid (11 μL, 50 mM solution, $5.5 \times 10^{-7}$ moles) and 4-tributylstannyl benzaldehyde (100 μL, 200 μg, 2 mg/mL solution in acetonitrile, $5.06 \times 10^{-7}$ moles). An additional 50 μL acetonitrile was added to aid solubility of the 4-tributylstannyl benzaldehyde, and the reaction mixture allowed to incubate at room temperature for approximately 20 minutes prior to HPLC analysis, which showed [$^{123}$I]-4-iodobenzaldehyde ($t_R$~8 minutes, system A, Example 2) with an RCP of >90%. To the reaction mixture was added 1 mL acetonitrile and 10 mL water and the resulting solution loaded onto a tC-18 light cartridge (pre-treated with 2.5 mL methanol and 5 mL water). [$^{123}$I]-4-iodobenzaldehyde was eluted with 0.5 mL 1:1 t-butanol:water in 48% yield (non-decay corrected).

Step (b): Preparation of Compound 3A

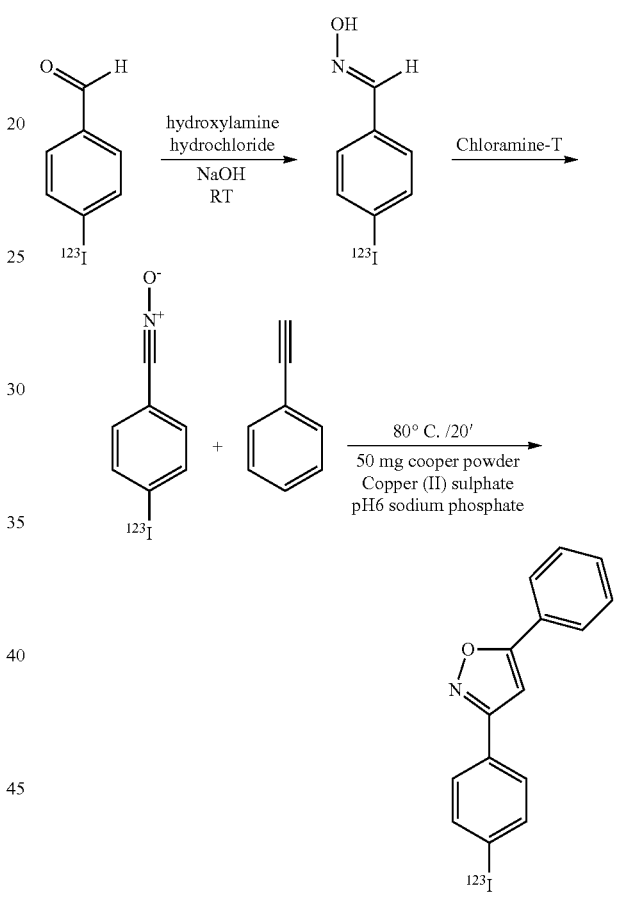

To purified [$^{123}$I]-4-iodobenzaldehyde (0.5 mL) in a wheaton vial was added hydroxylamine hydrochloride (74 μg, 18.5 μL of 4 mg/mL solution in water, $1.06 \times 10^{-6}$ moles) and sodium hydroxide (106.5 μg, 10.6 μL of 10 mg/mL solution in water, $2.65 \times 10^{-6}$ moles). The pH was measured at approximately 10 and the reaction mixture stirred at room temperature for 30 minutes. HPLC analysis confirmed an 81% conversion to a more hydrophilic species ($t_R$ 7.0 minutes, System A, Example 2) thought to be the oxime. To the crude oxime was added in the following order; chloramine-T trihydrate (750 μg, 7.5 μL of 100 mg/mL solution in water, $2.66 \times 10^{-6}$ moles), copper (II) sulfate (3.8 μg, 7.6 μL of 0.5 mg/mL solution in water, $1.53 \times 10^{-8}$ moles), −40 mesh copper powder (50 mg), sodium phosphate buffer (100 μL, pH 6, 50 mM) and phenylacetylene (0.64 mg in 0.1 mL DMF, $6.3 \times 10^{-6}$ moles). The pH of the reaction mixture was measured at 6 and the reaction mixture heated at 80° C. for 20 minutes. After cooling, a 10 μL sample was analysed by HPLC indicating formation of the desired product (HPLC $t_R$ 19.5 minutes, System A, Example 2) with an RCP of 11.6%. The crude preparation was diluted with 0.4 mL 0.1% TFA in acetonitrile and 0.4 mL 0.1% TFA in water and the desired product isolated by HPLC (System A, Example 2) in 3% yield (non decay corrected) with an RCP of 100%. Co-elution of the purified product with authentic Compound 3 (Example 5) was observed.

Example 7

Synthesis of Maleimide-Alkyne Bifunctional Linker (1)

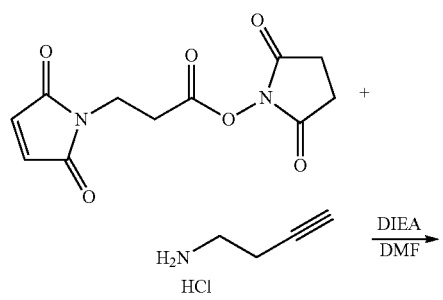

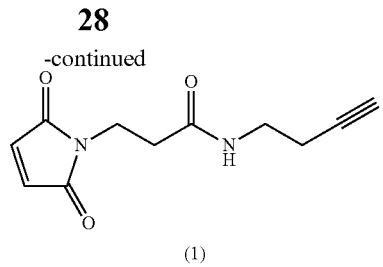

(1)

N-[β-Maleimidopropyloxy]succinimide ester (50 mg, 1.25 equiv) was dissolved in 1.0 mL of dry DMF. 3-Butyn-1-amine hydrochloride (16 mg, 1.0 equiv) was dissolved in 0.5 mL of dry DMF and 26 μL of diisopropylethylamine (DIEA). This amine solution was added drop-wise to the succinimide ester while keeping the ester solution in an ice bath. The mixture was stirred at 0° C. for 10 min. The solution was warmed up to room temperature and stirred for 18 h. The solvents were evaporated under vacuum and the residue was dissolved in 5 mL $CH_2Cl_2$. The organic solution was extracted with brine (3×5 mL) and dried over $MgSO_4$. The solvent was removed under reduced pressure and the crude material was purified using flash chromatography (silica, MeOH/$CH_2Cl_2$). The product (1) was purified from grease by dissolving the sample in a minimum amount of $CH_2Cl_2$ (ca. 2 mL), followed by three washes with hexanes. The product (1) precipitated as a fluffy white solid. Characterization of the product was achieved using $^1$H-NMR. Yield: 8.2 mg (25%).

$^1$H-NMR (500 MHz, $CDCl_3$): δ 2.02 (s, 1), 2.41 (t, J=5 Hz, 2), 2.57 (t, J=5 Hz, 2), 3.42 (td, J=5 Hz, 2), 3.88 (t, J=5 Hz), 5.90 (bs, 1), 6.73 (s, 2).

The invention claimed is:

1. A method of radioiodination of a biological targeting moiety, said method comprising:

(i) provision of a compound of Formula (I):

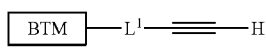
(I)

(ii) reaction of said compound of Formula (I) with a compound of Formula (IIa) or Formula (IIb):

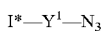
(IIa)

(IIb)

in the presence of a click cycloaddition catalyst, to give a conjugate of Formula (IIIa) or (IIIb) respectively:

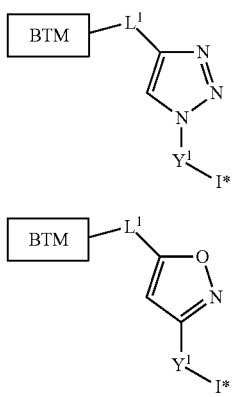
(IIIa)
(IIIb)

wherein:

I* is a radioisotope of iodine suitable for in vivo imaging, chosen from $^{123}I$, $^{124}I$ or $^{131}I$;

$L^1$ is a linker group which may be present or absent, wherein said linker group is of formula $-(A)_m-$ wherein each A is independently —$CR_2$—, —CR=CR—, —C≡C—, —$CR_2CO_2$—, —$CO_2CR_2$—, —NRCO—, —CONR—, —NR(C=O)NR—, —NR(C=S)NR—, —$SO_2NR$—, —$NRSO_2$—, —$CR_2OCR_2$—, —$CR_2SCR_2$—, —$CR_2NRCR_2$—, a $C_{4-8}$ cycloheteroalkylene group, a $C_{4-8}$ cycloalkylene group, a $C_{5-12}$ arylene group, or a $C_{3-12}$ heteroarylene group, an amino acid, a sugar or a monodisperse polyethyleneglycol (PEG) building block;

wherein each R is independently chosen from: H, $C_{1-4}$ alkyl, $C_{2-4}$ alkenyl, $C_{2-4}$ alkynyl, $C_{1-4}$ alkoxyalkyl or $C_{1-4}$ hydroxyalkyl;

and m is an integer of value 1 to 20;

$Y^1$ is —$Ar^1$— or —$X^1$—;

where —$Ar^1$— is $C_{3-10}$ arylene, and $X^1$— is —CH=CH—$(CH_2)_n(Ar^1)_j$— or —CH=CH—$(Ar^1)_j$—$(CH_2)_n$— where j is 0 or 1, and n is an integer of value 0 to 4, wherein when $Y^1$ is —$X^1$—, I* is attached to —CH=CH terminus of $X^1$;

BTM is the biological targeting moiety chosen from: a single amino acid, a 3-80 mer peptide, an enzyme substrate, an enzyme antagonist an enzyme agonist, an enzyme inhibitor or a receptor-binding compound; and wherein the compound of Formula (I) is generated by deprotection of a compound of Formula (Ia):

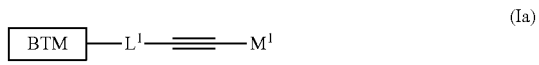
(Ia)

wherein $M^1$ is an alkyne-protecting group.

2. A method of radioiodination of a biological targeting moiety, said method comprising:

(i) provision of a compound of Formula (I):

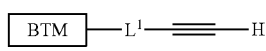
(I)

(ii) reaction of said compound of Formula (I) with a compound of Formula (IIa) or Formula (IIb):

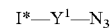
(IIa)

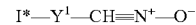
(IIb)

in the presence of a click cycloaddition catalyst, to give a conjugate of Formula (IIIa) or (IIIb) respectively:

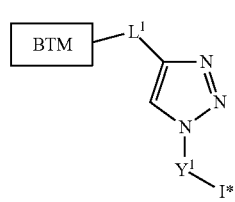
(IIIa)

-continued

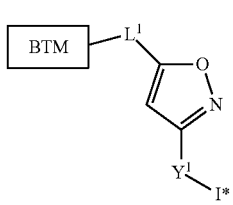
(IIIb)

wherein:
  I* is a radioisotope of iodine suitable for in vivo imaging, chosen from $^{123}$I, $^{124}$I or $^{131}$I;
  $L^1$ is a linker group which may be present or absent, wherein said linker group is of formula $-(A)_m-$ wherein each A is independently —CR$_2$—, —CR=CR—, —C≡C—, —CR$_2$CO$_2$—, —CO$_2$CR$_2$—, —NRCO—, —CONR—, —NR(C=O)NR—, —NR(C=S)NR—, —SO$_2$NR—, —NRSO$_2$—, —CR$_2$OCR$_2$—, —CR$_2$SCR$_2$—, —CR$_2$NRCR$_2$—, a $C_{4-8}$ cycloheteroalkylene group, a $C_{4-8}$ cycloalkylene group, a $C_{5-12}$ arylene group, or a $C_{3-12}$ heteroarylene group, an amino acid, a sugar or a monodisperse polyethyleneglycol (PEG) building block;
    wherein each R is independently chosen from: H, $C_{1-4}$ alkyl, $C_{2-4}$ alkenyl, $C_{2-4}$ alkynyl, $C_{1-4}$ alkoxyalkyl or $C_{1-4}$ hydroxyalkyl;
    and m is an integer of value 1 to 20;
  $Y^1$ is —Ar$^1$— or —X$^1$—;
    where —Ar$^1$— is $C_{3-10}$ arylene, and
    —X$^1$— is —CH=CH—(CH$_2$)$_n$— or —CH=CH—(Ar$^1$)$_j$—(CH$_2$)$_n$—
    where j is 0 or 1, and n is an integer of value 0 to 4,
    wherein when $Y^1$ is —X$^1$—, I* is attached to —CH=CH terminus of X$^1$;
  BTM is the biological targeting moiety chosen from: a single amino acid, a 3-80 mer peptide, an enzyme substrate, an enzyme antagonist an enzyme agonist, an enzyme inhibitor or a receptor-binding compound; and
wherein the compound of Formula (IIa) or (IIb) is generated as follows:
  reaction of a precursor of either Formula (IVa) or Formula (IVb) respectively:

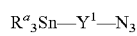
(IVa)

(IVb)

wherein $Y^1$ is as defined above, and each $R^a$ is independently $C_{1-4}$ alkyl;
  with a supply of radioactive iodide ion in the presence of an oxidising agent, to give the compound of Formula (IIa) or (IIb) respectively.

3. A method of radioiodination of a biological targeting moiety, said method comprising:
  (i) provision of a compound of Formula (I):

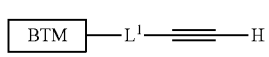
(I)

(ii) reaction of said compound of Formula (I) with a compound of Formula (IIa) or Formula (IIb):

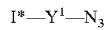
(IIa)

(IIb)

in the presence of a click cycloaddition catalyst, to give a conjugate of Formula (IIIa) or (IIIb) respectively:

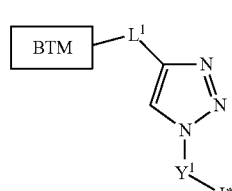
(IIIa)

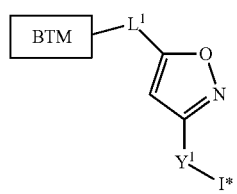
(IIIb)

wherein:
  I* is a radioisotope of iodine suitable for in vivo imaging, chosen from $^{123}$I, $^{124}$I or $^{131}$I;
  $L^1$ is a linker group which may be present or absent, wherein said linker group is of formula $-(A)_m-$ wherein each A is independently —CR$_2$—, —CR=CR—, —C≡C—, —CR$_2$CO$_2$—, —CO$_2$CR$_2$—, —NRCO—, —CONR—, —NR(C=O)NR—, —NR(C=S)NR—, —SO$_2$NR—, —NRSO$_2$—, —CR$_2$OCR$_2$—, —CR$_2$SCR$_2$—, —CR$_2$NRCR$_2$—, a $C_{4-8}$ cycloheteroalkylene group, a $C_{4-8}$ cycloalkylene group, a $C_{5-12}$ arylene group, or a $C_{3-12}$ heteroarylene group, an amino acid, a sugar or a monodisperse polyethyleneglycol (PEG) building block;
    wherein each R is independently chosen from: H, $C_{1-4}$ alkyl, $C_{2-4}$ alkenyl, $C_{2-4}$ alkynyl, $C_{1-4}$ alkoxyalkyl or $C_{1-4}$ hydroxyalkyl;
    and m is an integer of value 1 to 20;
  $Y^1$ is —Ar$^1$— or —X$^1$—;
    where —Ar$^1$— is $C_{3-10}$ arylene, and
    —X$^1$— is —CH=CH—(CH$_2$)$_n$—(Ar$^1$)$_j$— or —CH=CH—(Ar$^1$)$_j$—(CH$_2$)$_n$—
    where j is 0 or 1, and n is an integer of value 0 to 4,
    wherein when $Y^1$ is —X$^1$—, I* is attached to —CH=CH terminus of X$^1$;
  BTM is the biological targeting moiety chosen from: a single amino acid, a 3-80 mer peptide, an enzyme substrate, an enzyme antagonist an enzyme agonist, an enzyme inhibitor or a receptor-binding compound; and
which method is carried out in an aseptic manner, such that the product of Formula (IIa) or (IIIb) is obtained as a radiopharmaceutical composition.

4. A method of radioiodination of a biological targeting moiety, said method comprising:
  (i) provision of a compound of Formula (I):

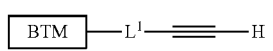
(I)

(ii) reaction of said compound of Formula (I) with a compound of Formula (IIa) or Formula (IIb):

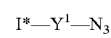
(IIa)

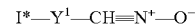
(IIb)

in the presence of a click cycloaddition catalyst, to give a conjugate of Formula (IIIa) or (IIIb) respectively:

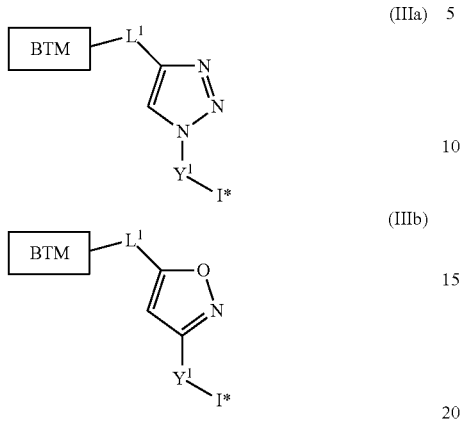

wherein:
I* is a radioisotope of iodine suitable for in vivo imaging, chosen from $^{123}$I, $^{124}$I or $^{131}$I;
$L^1$ is a linker group which may be present or absent, wherein said linker group is of formula $-(A)_m-$ wherein each A is independently $-CR_2-$, $-CR=CR-$, $-C\equiv C-$, $-CR_2CO_2-$, $-CO_2CR_2-$, $-NRCO-$, $-CONR-$, $-NR(C=O)NR-$, $-NR(C=S)NR-$, $-SO_2NR-$, $-NRSO_2-$, $-CR_2OCR_2-$, $-CR_2SCR_2-$, $-CR_2NRCR_2-$, a $C_{4-8}$ cycloheteroalkylene group, a $C_{4-8}$ cycloalkylene group, a $C_{5-12}$ arylene group, or a $C_{3-12}$ heteroarylene group, an amino acid, a sugar or a monodisperse polyethyleneglycol (PEG) building block;
wherein each R is independently chosen from: H, $C_{1-4}$ alkyl, $C_{2-4}$ alkenyl, $C_{2-4}$ alkynyl, $C_{1-4}$ alkoxyalkyl or $C_{1-4}$ hydroxyalkyl;
and m is an integer of value 1 to 20;
$Y^1$ is $-Ar^1-$ or $-X^1-$;
where $-Ar^1-$ is $C_{3-10}$ arylene, and
$-X^1-$ is $-CH=CH-(CH_2)_j-$ or $-CH=CH-(Ar^1)_j-(CH_2)_n-$
where j is 0 or 1, and n is an integer of value 0 to 4,
wherein when $Y^1$ is $-X^1-$, I* is attached to $-CH=CH$ terminus of $X^1$;
BTM is the biological targeting moiety chosen from: a single amino acid, a 3-80 mer peptide, an enzyme substrate, an enzyme antagonist an enzyme agonist, an enzyme inhibitor or a receptor-binding compound; and
which method is carried out using an automated synthesizer apparatus.

5. A radiopharmaceutical composition comprising an effective amount of a compound of Formula (IIIa) or (IIIb), together with a biocompatible carrier medium:

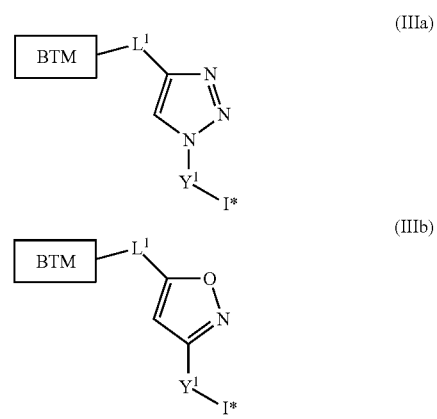

wherein:
I* is a radioisotope of iodine suitable for in vivo imaging, chosen from $^{123}$I, $^{124}$I or $^{131}$I;
$L^1$ is a linker group which may be present or absent, wherein said linker group is of formula $-(A)_m-$ wherein each A is independently $-CR_2-$, $-CR=CR-$, $-C\equiv C-$, $-CR_2CO_2-$, $-CO_2CR_2-$, $-NRCO-$, $-CONR-$, $-NR(C=O)NR-$, $-NR(C=S)NR-$, $-SO_2NR-$, $-NRSO_2-$, $-CR_2OCR_2-$, $-CR_2SCR_2-$, $-CR_2NRCR_2-$, a $C_{4-8}$ cycloheteroalkylene group, a $C_{4-8}$ cycloalkylene group, a $C_{5-12}$ arylene group, or a $C_{3-12}$ heteroarylene group, an amino acid, a sugar or a monodisperse polyethyleneglycol (PEG) building block;
wherein each R is independently chosen from: H, $C_{1-4}$ alkyl, $C_{2-4}$ alkenyl, $C_{2-4}$ alkynyl, $C_{1-4}$ alkoxyalkyl or $C_{1-4}$ hydroxyalkyl;
and m is an integer of value 1 to 20;
$Y^1$ is $-Ar^1-$ or $-X^1-$;
where $-Ar^1-$ is $C_{3-10}$ arylene, and
$-X^1-$ is $-CH=CH-(CH_2)_n-(Ar^1)_j-$ or $-CH=CH-(Ar^1)_j-(CH_2)_n-$
where j is 0 or 1, and n is an integer of value 0 to 4,
wherein when $Y^1$ is $-X^1-$, I* is attached to $-CH=CH$ terminus of $X^1$;
BTM is the biological targeting moiety chosen from: a single amino acid, a 3-80 mer peptide, an enzyme substrate, an enzyme antagonist an enzyme agonist, an enzyme inhibitor or a receptor-binding compound.

\* \* \* \* \*